US010182897B2

(12) United States Patent
Bercovich et al.

(10) Patent No.: US 10,182,897 B2
(45) Date of Patent: *Jan. 22, 2019

(54) FEMALE URINARY INCONTINENCE DEVICE

(71) Applicant: GYNAMICS WOMEN'S HEALTH LTD., Ramat Yishay (IL)

(72) Inventors: Eyal Bercovich, Haifa (IL); Ronen Raveh, Ramat Yishay (IL)

(73) Assignee: GYNAMICS WOMEN'S HEALTH LTD., Ramat Yishay (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/410,903

(22) Filed: Jan. 20, 2017

(65) Prior Publication Data

US 2017/0128183 A1    May 11, 2017

Related U.S. Application Data

(63) Continuation of application No. 14/349,348, filed as application No. PCT/IL2011/000771 on Oct. 4, 2011, now Pat. No. 9,549,802.

(51) Int. Cl.
*A61F 2/00* (2006.01)
*A61F 6/08* (2006.01)

(52) U.S. Cl.
CPC ............ *A61F 2/005* (2013.01); *A61F 2/0027* (2013.01); *A61F 6/08* (2013.01);
(Continued)

(58) Field of Classification Search
CPC ........ A61F 2/00; A61F 2/0004; A61F 2/0009; A61F 2/005; A61F 2/0013; A61F 2/0022;
(Continued)

(56) References Cited

U.S. PATENT DOCUMENTS

| 5,603,685 A | 2/1997 | Tutrone, Jr. |
| 5,609,559 A | 3/1997 | Weitzner |

(Continued)

FOREIGN PATENT DOCUMENTS

| WO | 9601084 A1 | 1/1996 |
| WO | 2004103213 A1 | 12/2004 |

(Continued)

OTHER PUBLICATIONS

International Search Report for corresponding PCT application, dated Feb. 13, 2012, 4 pages.

*Primary Examiner* — Kaylee Wilson
*Assistant Examiner* — Carrie R Dorna
(74) *Attorney, Agent, or Firm* — Roach Brown McCarthy & Gruber, P.C.; Kevin D. McCarthy

(57) ABSTRACT

A device is provided for applying pressure on a vaginal wall of a female subject, said device being configured for insertion into a vaginal cavity of said female subject. The device includes a first deformable element, a second deformable element and a transmission element. The first deformable element has a resting-state and at least one deformed state and is configured for undergoing deformation in response to an inner body pressure. When in the resting state, the first deformable element is configured to anchor the device inside the vaginal cavity. The second deformable element has a resting-state and at least one deformed state, and is configured for undergoing deformation to apply a second pressure on the vaginal wall, such second pressure being operable to narrow a urethral portion the female subject. The transmission element has a first end connected to the first deformable element and a second end connected to the second deformable element, and is configured for converting the deformation of the first deformable element to a deformation of the second deformable element, and for returning the first and (Continued)

second deformable elements to their respective resting states.

14 Claims, 15 Drawing Sheets

(52) U.S. Cl.
CPC .......... *A61F 2230/0078* (2013.01); *A61F 2250/0003* (2013.01); *A61F 2250/0013* (2013.01); *A61F 2250/0048* (2013.01)

(58) Field of Classification Search
CPC .......... A61F 2/0027; A61F 2/004; A61F 6/06; A61F 6/08
See application file for complete search history.

(56) References Cited

U.S. PATENT DOCUMENTS

| | | | |
|---|---|---|---|
| 6,095,969 A | | 8/2000 | Karram et al. |
| 6,096,057 A | * | 8/2000 | Klingenstein ............ A61F 2/005 606/197 |
| 2004/0158122 A1 | | 8/2004 | Guerquin |
| 2008/0291149 A1 | | 11/2008 | Sinai |

FOREIGN PATENT DOCUMENTS

| | | | |
|---|---|---|---|
| WO | WO2008063085 | * | 5/2008 |
| WO | 2011121591 A2 | | 10/2011 |

* cited by examiner

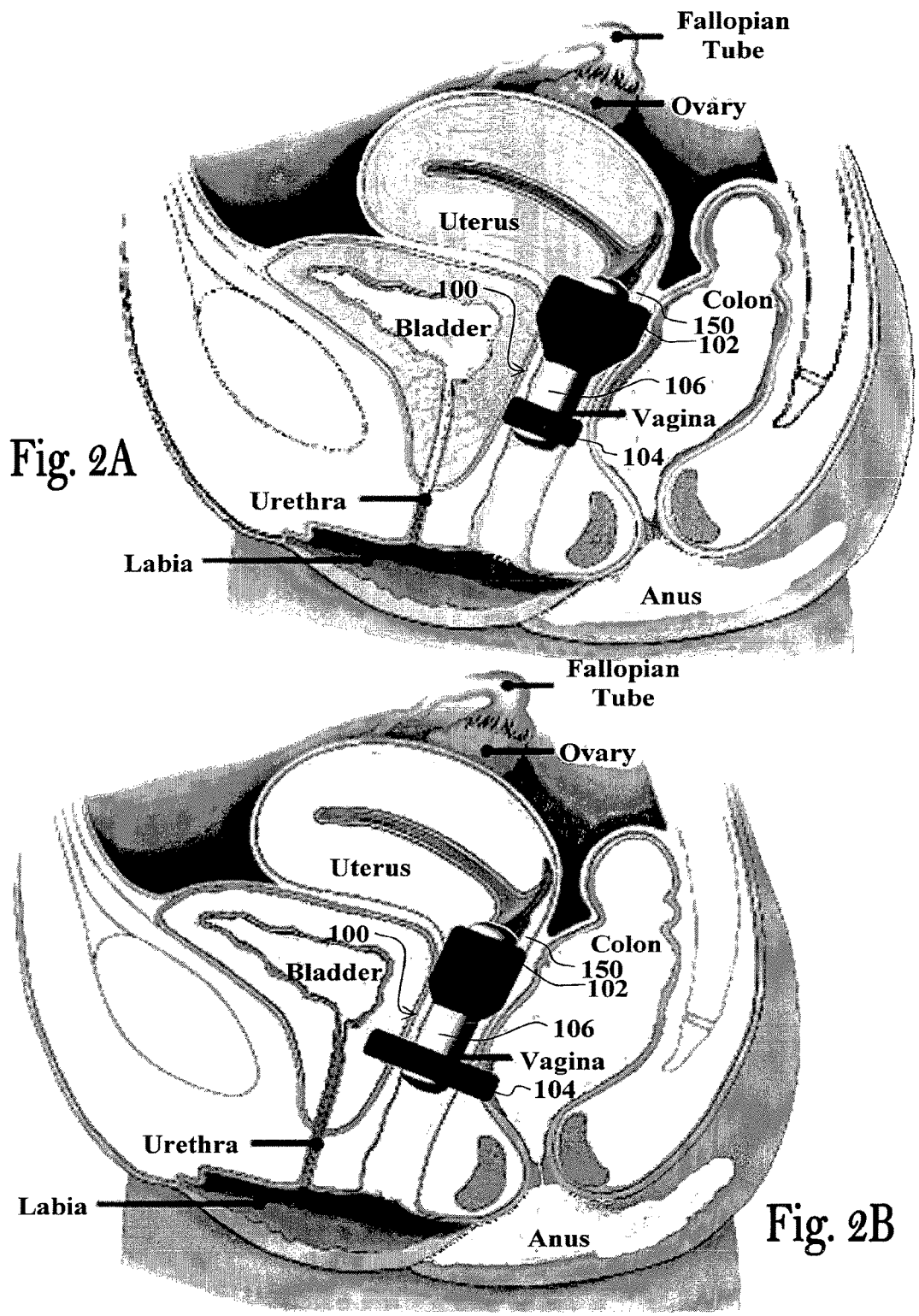

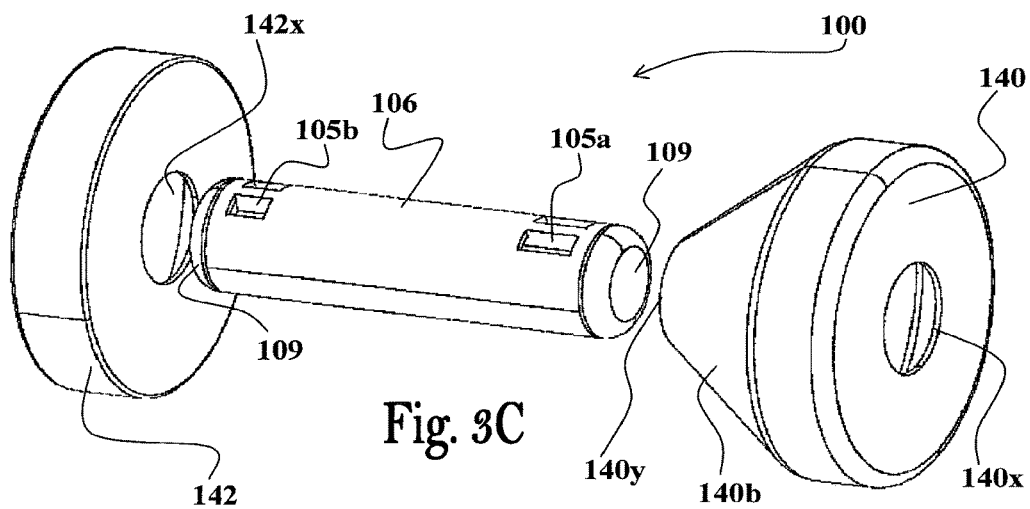
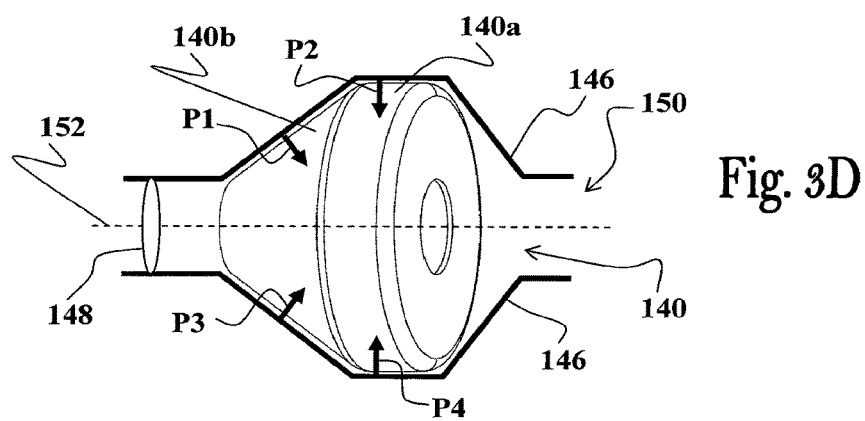

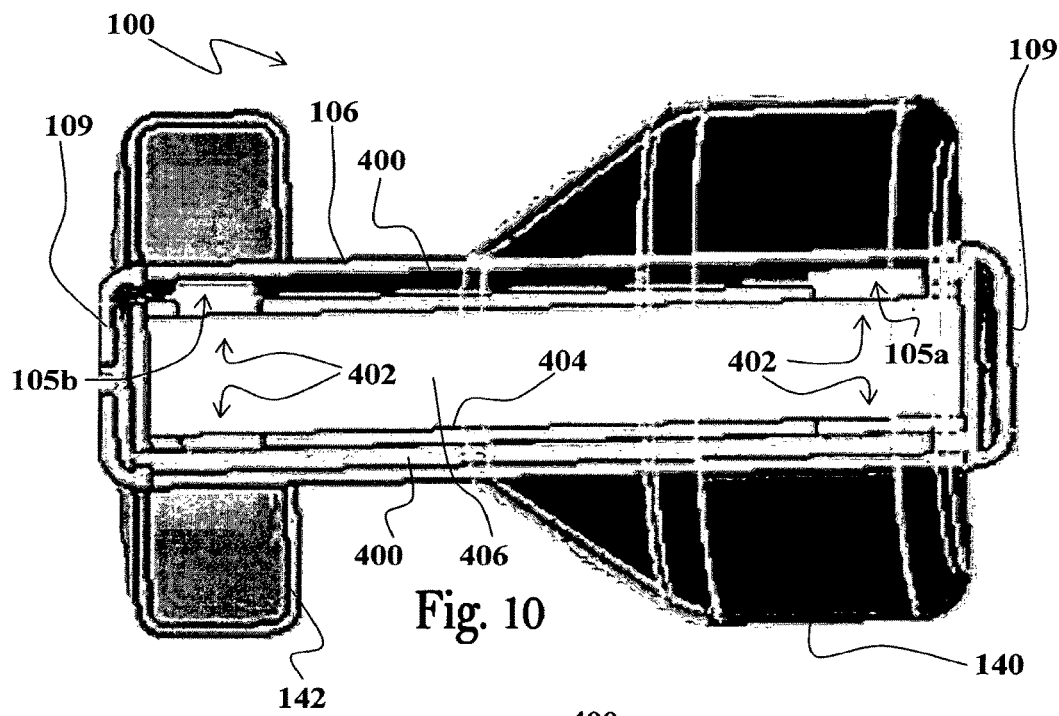
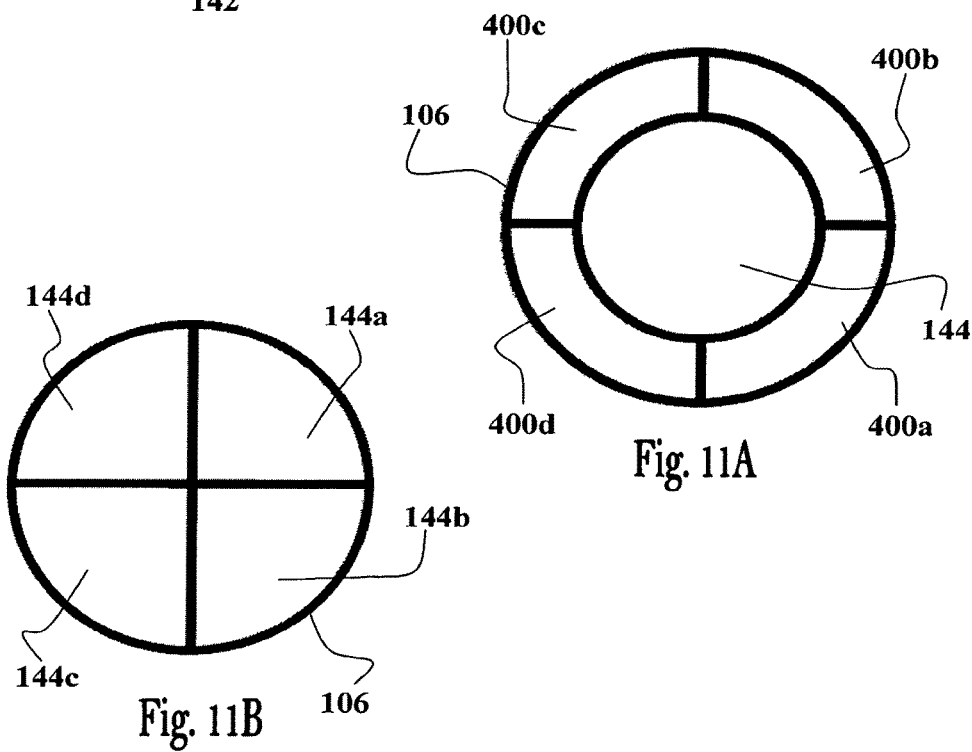

FEMALE URINARY INCONTINENCE DEVICE

REFERENCE TO APPLICATIONS

This application claims priority as a continuation of Ser. No. 14/349,348, filed on Apr. 3, 2014 (U.S. Pat. No. 9,549,802); which claims priority as a 371 application of international patent application serial number PCT/IL2011/000771, filed on Oct. 4, 2011.

FIELD OF THE INVENTION

The present invention relates in general to a technique for treating and/or reducing urinary incontinence and urinary tract infection in females. In particular, it relates to devices that are inserted into the vagina and are capable of being activated by intra vaginal pressure, intra-abdominal pressure or contraction of the pelvic floor muscles to transmit a transient pressure on the urethra.

BACKGROUND OF THE INVENTION

Urinary incontinence (UI), the involuntary loss of urine, is estimated to affect approximately one in three adult women. Due to such factors as pregnancy and childbirth, menopause, and the structure of the female urinary tract, UI is twice as prevalent in women as in men. UI can also arise from such causes as neurologic injury, birth defects, stroke, multiple sclerosis, and due to physical problems associated with aging and overweight. UI can run the gamut from slightly bothersome to completely debilitating: some women suffering from UI lose a few drops of urine during activities such as running or coughing, while others may feel a strong, sudden urge to urinate just before losing a large amount of urine. For some women suffering from UI, the risk of public embarrassment can keep them from enjoying activities with family and friends.

Stress urinary incontinence (SUI), also known as effort incontinence, is typified by loss of small amounts of urine associated with movements that increase the intra-abdominal pressure, thereby increasing the pressure on the bladder. If the support provided to the urethra by the fascia of the pelvis is insufficient, the two main mechanisms that cause SUI are weakening of connective tissue (fascia) and sphincter dysfunction. In these cases SUI typically occurs at times of increased intra-abdominal pressure, for example, during movements such as coughing, laughing, sneezing, and exercise that increase the intra-abdominal pressure. Such increased intra-abdominal pressure causes the pressure on the urinary bladder to increase, but due to the insufficient urethra support the urethral pressure remains unchanged, which allows urine to pass through the urethra.

While SUI is not an inevitable consequence of aging, SUI is more common in older women than in younger women. This is because striated muscle fibers and the firmness of the endopelvic fascia decrease with age, thereby decreasing the effectiveness of the sphincteric and support systems.

A problem that may be parallel to or independent of UI is recurring urinary tract infection (UTI). UTI is frequently caused by the entrance of infectious microorganisms such as bacteria or yeast into the urinary tract. These microorganisms then traverse or partially traverse the urinary tract and lead to infection. This problem is especially acute in women who suffer from UI, since compression (closure) of their urethras is compromised.

A vaginal female incontinence device including an annular ring-shaped inflatable body is described in U.S. Pat. No. 5,007,894 to Enhorning. This incontinence device includes two projections configured to support the tissue of the vaginal wall, lateral and adjacent each side of the upper urethra, such that the tissue therebetween be sideways stretched to offer counter pressure to sudden increases in intra-abdominal pressure. This ring-shaped device can only be placed inside the vagina in a specific orientation, which thus requires a certain degree of proficiency for inserting it and probably also frequent refitting to place the urethra along the midline of the device between the two projections. Additionally, this device is not configured to apply direct pressure on the vaginal tissue under the urethra. It therefore understood that the placement of this annular ring-shaped device requires a practitioner, and doubtfully if a user can place it correctly inside the vagina without such assistance, and if such ring-shaped design and dimensions can provide comfort and convenience in use.

General Description

As the population ages, and the effectiveness of the sphincteric and support systems decreases, SUI and UTI have become more common problems, that are not only age related. For example, it is now understood that SUI and UTI also occur due overweight, and lately it has become common knowledge that SUI occurs at a younger age, more than what was reported so far, that is due to greater openness to the subject. Therefore, there is an increasing need for non-surgical methods for treating or decreasing occurrences of SUI and/or UTI.

In some embodiments the present invention provides for temporary and dynamic application of pressure over one or more portions of the vaginal wall adjacent to an upper section of the urethra, in response to forces exerted on the upper portions of the vagina and/or in the abdomen. Therefore, the present invention in some of its embodiments may be used to provide a temporary and dynamic constriction of one or more portions of the urethra, in response to inner body stimulus. Such a stimulus may be, for example, an involuntary increase of inter-abdominal or intra-vaginal pressure, for example due to a factor, such as a cough, a laugh, a sneeze, or exercise. The stimulus may also be a voluntary contraction of the pelvic floor muscles.

Therefore, according to some embodiments of the present invention, there is provided a device for insertion into a vaginal cavity of a female subject and configured to apply a temporary and dynamic pressure over one or more portions of the urethral wall, in response to an inner body stimulus. The device includes a first deformable element, a second deformable element, and a transmission element interconnecting said deformable elements.

The first deformable element may be configured for being located in a resting-state in proximity of the cervix and for receiving a pressure (hereinafter first pressure) created by an intra-vaginal pressure, and/or an intra-abdominal pressure, and/or a contraction of the pelvic floor muscles. In some embodiments the state of the first deformable element is changed into a deformed-state when such first pressure is applied thereon. Possibly, the state of the first deformable element is changed into a deformed-state when such first pressure is higher than a predetermined first threshold pressure.

The second deformable element may be configured for being located in a resting-state near an upper section of the urethra, between the first deformable element and the opening of the vagina (i.e., the external opening of the vagina—the vaginal entrance). In some embodiments the second deformable element is designed to change into a deformed-state in response to the deformation of the first deformable element, in order to apply a second pressure over one or more portions of the urethral wall. This second pressure is utilized to narrow portions of the urethra receiving the applied second pressure.

More particularly, the second deformable element is configured to exert pressure on the vaginal wall which in turn exerts pressure on a portion of the urethra in its proximity. In some embodiments of the present invention the device is configured such that the second deformable element is located adjacent to a portion of the urethra that is between the beginning of the urethra (bladder neck) and an approximate region that is referred to as midurethra.

The transmission element has a first end connected to the first deformable element and a second end connected to the second deformable element, and is designed for converting a deformation of said first deformable element to a deformation of said second element. In some embodiments of the invention the conversion carried out by the transmission element is implemented by controllably transferring pressure from the first deformable element to the second deformable element. In some embodiments the transmission element is further configured to restore the states of the first and second deformable elements back into their respective resting-states. Optionally, the transmission element is configured to restore the states of the first and second deformable elements back into their respective resting-states when the first pressure becomes smaller than a predetermined second threshold pressure. In some embodiments of the present invention the transmission element is configured to convert the deformation of the first deformable element whenever the first pressure is greater than the first threshold pressure. In some embodiments the first threshold pressure is equal to the second threshold pressure.

Though the transmission element may be a stiff element, in some possible embodiments the transmission element is made from a soft or bendable material allowing it a degree of flexibility for adjusting its shape when placed inside the vagina. Thus, the device of the present invention may be comprised form two deformable elements, as described hereinabove and hereinbelow, interconnected by a bendable transmission element, which may render the device more comfortable and thus more convenient for use.

As explained above, an involuntary increase of intra-vaginal or intra-abdominal pressure typically corresponds to an increase in bladder pressure, which may result in urine loss. Therefore, the device in some embodiments of the present invention converts an increase of intra-vaginal or intra-abdominal pressure to an increase of pressure on the vaginal wall, in order to increase the urethral pressure, and preferably keep the urethral pressure higher than the bladder pressure. Thus, in order to prevent urine leak, pressure is applied by the device of the present invention over the vaginal wall to narrow or occlude the urethra whenever bladder pressure rises as a result of an increase of intra-vaginal or intra-abdominal pressure. Accordingly, in some embodiments the device of the present invention is configured such that stronger intra-vaginal and/or intra-abdominal pressures are translated by the device to a stronger pressure that the second deformable element exerts on the vaginal wall and thereby on the upper portion of the urethra. Thus, the device of the present invention may be able to modulate the pressure on the urethra needed to diminish or even prevent SUI.

The term urethral pressure ($P_{urethral}$) used herein to refer to the pressure inside the urethra (usually measured during a urodynamic test). The term bladder pressure ($P_{bladder}$) used herein to refer to the sum of the pressure of the wall of the bladder and the intra-abdominal pressure exerted on the bladder. In this sense SUI typically occurs when $P_{urethral} < P_{bladder}$.

The term resting-state used herein to refer to the state of the device and its deformable elements before the first pressure is applied on the first deformable element. In other words, in the resting-state the deformable elements of the device of the present invention are not in a deformed state, such that the device is not narrowing/occluding the urethra in the resting-state.

In some possible embodiments of the present invention when the pressure exerted on the first deformable element of the device decreases the pressure applied on the vaginal wall by the second deformable elements is also decreased. In this way, simultaneously as the first pressure extinguishes also does the pressure applied by the second deformable element of the device. Therefore, once the first pressure is extinguished the first and second deformable elements restore their respective resting-states such that the pressure applied by the second deformable element on the urethra wall (if any) is not sufficiently high to occlude the urethra.

In some embodiments of the present invention the device is configured such that any pressure sensed by the first deformable element immediately result in changing its state into a deformed stated (i.e., the first pressure is not required to be greater than some predetermined threshold pressure). Accordingly, in such possible embodiments the device of the present invention is configured to react to any inner body pressure (also referred to herein as a first pressure) sensed by the first deformable element. Similarly, in possible embodiments of the present invention the deformable elements may restore their resting-states shortly after the pressure sensed by the first deformable element is vanished or substantially diminished (without requiring the first pressure to be smaller than some predetermined second pressure threshold).

In possible embodiments of the present invention the device is configured such that a small amount of pressure is applied over the vaginal wall even when the deformable elements are in their resting-states. This may serve to create a certain friction between the second deformable element and the vaginal wall, thereby anchoring the device within the vaginal cavity. The device of the present invention may be configured such that if bladder pressure rises due to high volume of urine contained in the bladder, the pressure (if any) applied by the device on the vaginal wall remain unchanged, as long as the intra-vaginal or intra-abdominal pressure does not rise above the predetermined first threshold pressure. In this manner, the presence of the device of the present invention in the vaginal cavity of a female subject does not preclude her from urinating normally.

According to a preferred embodiment of the present invention, the first deformable element includes a first balloon, the second deformable element includes a second balloon, and the transmission element includes at least one hollow channel. Optionally, a fluid material may be contained in the device (e.g., gas or liquid). For example, the first balloon and the second balloon may be interconnected by the transmission element in hermetic fluid communication. In this manner, when the first pressure applied on the first balloon is higher than the predetermined threshold pressure, the first balloon deflates and causes some fluid to move from the first balloon through the hollow channel and into the second balloon. As a result, the second balloon is inflated and applies the second pressure on the vaginal wall, to narrow or occlude the urethra. In this example, when the first pressure falls below the predetermined first threshold pressure, the first balloon returns to its resting-state as some fluid is moved from the second balloon to the first balloon. In this manner, the second balloon deflates back into its resting-state, thereby decreasing, or completely canceling, the pressure applied by it on the vaginal wall.

In some exemplary embodiments, the device of the present invention can be used as a tool for exercising the pelvic floor muscles. In these exemplary embodiments the first deformable element can be deformed by a voluntary contraction of the pelvic floor muscles, and between contractions, the first deformable element restores its resting-state, allowing for further contractions to be made. Exercise of the pelvic floor muscles may contribute a strengthening thereof, which in turn may have various benefits including prevention of SUI, and prevention of organ prolapse.

According to some embodiments of the present invention, the second balloon is configured such that during its inflation, an increase of the second balloon's cross sectional area begins at one edge of the second balloon, and gradually propagates along a central axis thereof toward a second edge of the second balloon. In this manner the second balloon may apply the second pressure to a progressively longer portion of the urethral wall. If the direction of propagation of the increase of the cross sectional area of the second balloon is in the upward direction (i.e. the direction from the opening of the vagina to the cervix), any urine that may have been expelled from the urethra prior to the second balloon's inflation is pushed back into the bladder. On the other hand, if the direction of such propagation is downward (i.e., in the direction of the opening of the vagina), an infectious agent located in the urethra is expelled from the urethra, thereby preventing UTI.

In another aspect the present invention is directed to a method for preventing or reducing urinary incontinence in females, the method comprising introducing a device having a first deformable element, a second deformable element and a transmission element interconnecting said deformable elements, via an opening of a vagina of a female cavity, said deformable elements having a resting-state and at least one deformable state, advancing said device inside the vaginal cavity and positioning the first deformable element in proximity of the cervix such that said second deformable element is positioned over a portion of the vaginal wall proximal to an upper portion of the urethra, permitting said first deformable element to undergo deformation in response to an inner body pressure applied thereon, transferring at least some of the applied pressure via said transmission element to said second deformable element thereby causing said second deformable element to become deformed against said vaginal wall, thereby narrowing or occluding the urethra of the female subject.

Therefore, according to an aspect of some embodiments of the present invention, there is provided a device for applying pressure on a vaginal wall of a female subject, said device being configured for insertion into a vaginal cavity of said female subject. The device includes a first deformable element, a second deformable element and a transmission element. The first deformable element has a resting-state and at least one deformed state and is configured for undergoing deformation in response to an inner body pressure. When in the resting state, the first deformable element is configured to anchor the device inside the vaginal cavity. The second deformable element has a resting-state and at least one deformed state, and is configured for undergoing deformation to apply a second pressure on the vaginal wall, such second pressure being operable to narrow a urethral portion of the female subject. The transmission element has a first end connected to the first deformable element and a second end connected to the second deformable element, and is configured for converting the deformation of the first deformable element to a deformation of the second deformable element, and for returning the first and second deformable elements to their respective resting states.

Optionally, the first deformable element is configured to undergo deformation whenever the inner body pressure is greater than a threshold pressure.

In a variant, the inner body pressure is originated by at least one of: an intra-vaginal pressure, an intra-abdominal pressure, and a contraction of the pelvic floor muscles.

In another variant, the first deformable element is configured to be placed in proximity of a cervix of the female subject, and the second deformable element is configured to be placed in contact with the vaginal wall proximal to a section of the urethra.

In a further variant, the first and second deformable elements comprise a first and a second balloon, respectively, and the transmission element comprises at least one hollow channel traversable by a fluid, such that said fluid can flow between said balloons therethrough. The deformation of the first balloon caused by the inner body pressure is a deflation, and the deformation of the second balloon is an inflation.

Optionally, the first balloon comprises a tapering section configured to provide the anchor to the vaginal cavity. The tapering section faces the second balloon and narrows in the direction of the second balloon.

In a variant, the second balloon is configured to inflate such that successive portions thereof radially expand in a gradual manner in response to the first pressure from the first balloon. The radial expansions may define a progressive radial inflation propagating in a direction away from the first balloon or in a direction toward the first balloon.

In another variant, the first balloon has a cylindrical section configured for receiving the first pressure via a circumferential contact with a vaginal wall.

In yet another variant, the first balloon has a dome-shaped section at an end thereof facing away from said transmission element. Optionally, the dome-shaped section is configured for receiving at least a portion of the first pressure via a contact with an uterus of the female subject.

According to some embodiments of the present invention, the above device comprises at least one support element attached to at least the second balloon. The support element may be adapted to affect a shape of at least a portion of the second balloon.

Optionally, the transmission element is configured such that fluid flow rate therethrough in direction from the first balloon to the second balloon is different from fluid flow rate therethrough in direction from the second balloon to the first balloon. In some embodiments, the rate of fluid flow in the direction from the first balloon to the second balloon is greater than the rate of fluid flow in the direction from the second balloon to the first balloon.

In a variant, the transmission element comprises an inner channel surrounded by an outer channel. In another variant, the transmission element comprises an outer channel surrounding an inner element closed to said fluid. The outer channel may be divided into a plurality of sub-channels, each sub-channel being in fluid communication with said first and second balloons. These sub-channels may be configured to affect different fluid flow rates between the first and second balloon and in the reverse direction, such as for obtaining a faster inflation of the second balloon and slowing down its deflation.

Optionally, the above device comprises a valve in at least one of the sub-channels. The valve enables fluid passage from the first balloon to the second balloon and prevents, or resists, fluid passage from the second balloon to the first balloon, such that a deflation speed of the first balloon is higher than an inflation speed thereof.

In a variant, the above device comprises at least one valve covering most of the outer channel's cross sectional surface. The valve enables fluid passage from the first balloon to the second balloon and prevents or resists fluid passage from the second balloon to the first balloon, such that a deflation speed of the first balloon is higher than an inflation speed thereof.

In another variant, at least one of the above-mentioned channels is associated with a valve enabling fluid passage from the first balloon to the second balloon and preventing or resisting fluid passage from the second balloon to the first balloon, such that a deflation speed of the first balloon is higher than an inflation speed thereof.

In yet another variant, the transmission element comprises a first and second channel. The first channel is associated with a valve enabling fluid passage from the first balloon to the second balloon and preventing or resisting fluid passage from the second balloon to the first balloon, such that a deflation speed of the first balloon is higher than an inflation speed thereof.

Optionally, the transmission element has an outer valve configured for being connected to an applicator, such that upon connection with the applicator, the outer valve enables insertion of the fluid into the transmission element via the applicator, and removal of the fluid from the transmission element via the applicator.

In a variant, the transmission element includes an inner channel surrounded by an outer channel, such that a wall separating the inner channel from the outer channel has an aperture located near a first end of the transmission element. The device comprising a piston configured for travelling within the inner channel along a central axis of the inner channel, such that: the piston's travel toward the first balloon pushes the fluid from the inner channel into the outer channel and into the balloons via the aperture; the piston's travel toward the second balloon drains the fluid from the outer channel and from the balloons into the inner channel via said aperture; and the piston completely covers the aperture, when located at an edge of the inner channel proximal to the first end of said transmission element.

In a variant, the piston comprises a shaft configured for being pulled and pushed by a user, said shaft extending away from said piston to exit said transmission element via a second end of said transmission element.

Another aspect of the present invention relates to a device for narrowing a urethra of a female subject, the device being configured for being inserted and anchored in a resting-state inside a vaginal cavity of said female subject. The device includes a first balloon, a second balloon, and a tube. The first balloon is configured for being deflated in response to an inner body pressure. The second balloon configured for being inflated to apply a second pressure to the vaginal wall, thereby narrowing the urethra. The tube has at least one channel, and has a first end connected to the first balloon and a second end connected to the second balloon. The channel is configured to transfer a fluid from the first balloon to the second balloon and from the first balloon to the second balloon. In this manner a deflation of one of the balloons results in an inflation of the other one of the balloons, and an inflation of one of the balloons results in a deflation of the other one of the balloons.

Optionally, the first balloon is configured to be placed within the vaginal cavity, in proximity of the patient's cervix, and the second balloon is configured to be placed within the vaginal cavity between said first element and the vaginal entrance, and being in contact with the vaginal wall proximal to a section of the urethra.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A and 1B are block diagrams exemplifying a urethra-narrowing operation according to some embodiments of the present invention, wherein FIG. 1A shows the urethra before the narrowing and FIG. 1B after the narrowing;

FIGS. 2A and 2B schematically illustrate operation of a possible device of the present invention within a vaginal cavity, wherein FIG. 2A shows the device in a resting-state and FIG. 2B shows the device after deformations of its deformable elements;

FIGS. 3A to 3D exemplify an embodiment of the present invention wherein the first and second deformable elements of the device are inflatable and deflatable balloons, wherein FIG. 3A shows a perspective view of the device, FIG. 3B shows an exploded perspective view of the device without sealing caps, FIG. 3C shows an exploded perspective view of the device with the sealing caps, and FIG. 3D exemplifies forces applied over the first balloon due to the first pressure;

FIGS. 4A to 4C are schematic drawings illustrating an exemplary embodiment of the invention in which the device of the present invention is used to expel an infectious agent from the urethra, wherein FIG. 4A shows a sectional view of the device as deformation of the second balloon starts, FIG. 4B shows a sectional view illustrating the device as its second balloon becomes further longitudinally deformed, and FIG. 4C is a sectional view illustrating the device as the longitudinal deformation of the second balloon is completed;

FIGS. 5A to 5D are schematic illustrations of an example in which the device of the present invention is used to return some urine, that may have escaped the bladder, back into the bladder, wherein FIG. 5A shows the device as deformation of the second balloon starts, FIG. 5B shows the device as its second balloon becomes further longitudinally deformed, FIG. 5C shows the device as the longitudinal deformation of the second balloon is completed, and FIG. 5D shows a perspective sectional view of an embodiment of the present invention in which the balloons are configured to provide a "bowtie" balloon arrangement;

FIGS. 6A to 6C are schematic illustrations of an exemplary device of the present invention, in which the first balloon is configured for receiving both a circumferential pressure from contact with the vaginal wall and a longitudinal pressure from contact with the uterus, wherein FIG. 6A shows a perspective view of the device, FIG. 6B shows a sectional perspective view of the device, and FIG. 6C shows cross-sectional views of various parts of the device;

FIGS. 7A and 7B illustrate a device of the present invention, in which radial supports are used to define a shape of the second balloon, wherein FIG. 7A shows a perspective view of the device and FIG. 7B shows a sectional perspective view of the device;

FIG. 10 schematically illustrates a side sectional view of the another possible embodiment of the device of the present invention, in which the device comprises an outer channel surrounding a solid inner element;

FIG. 11A is a cross-sectional view of a transmission unit in one possible embodiment of the present invention, in which the outer channel is divided into a plurality of sub-channels;

FIG. 11B is a cross-section view of a transmission unit according to one possible embodiment of the present invention, in which the a channel passing through the transmission element is divided into a plurality of sub-channels;

FIGS. 12 to 15 schematically illustrate different examples of a device of the present invention configured to permit different rates of fluid flow in the direction from the first balloon to the second balloon and in the direction from the second balloon to the first balloon, wherein FIG. 12 shows a sectional view of a device having two separate parallel fluid channels communicating between the balloons, FIG. 13 shows a sectional perspective view of a device having concentric fluid channels and a valve inside the inner channel, FIG. 14 shows the device of FIG. 13 with a valve in its outer lumen, and FIG. 15 shows a perspective cross-sectional view of the device of FIG. 14 which outer channel is divided into four fluid sub-channels some of which having valves in them;

FIGS. 17A and 17D schematically illustrate a device of the present invention inflatable by a movable piston element, wherein FIG. 17A shows the device before inflation, FIG. 17D shows the device after completing the inflation.

It is noted that the embodiments exemplified in the figures are not intended to be in scale and are in diagram form to facilitate ease of understanding and description.

DETAILED DESCRIPTION OF EMBODIMENTS

Figure 1A:
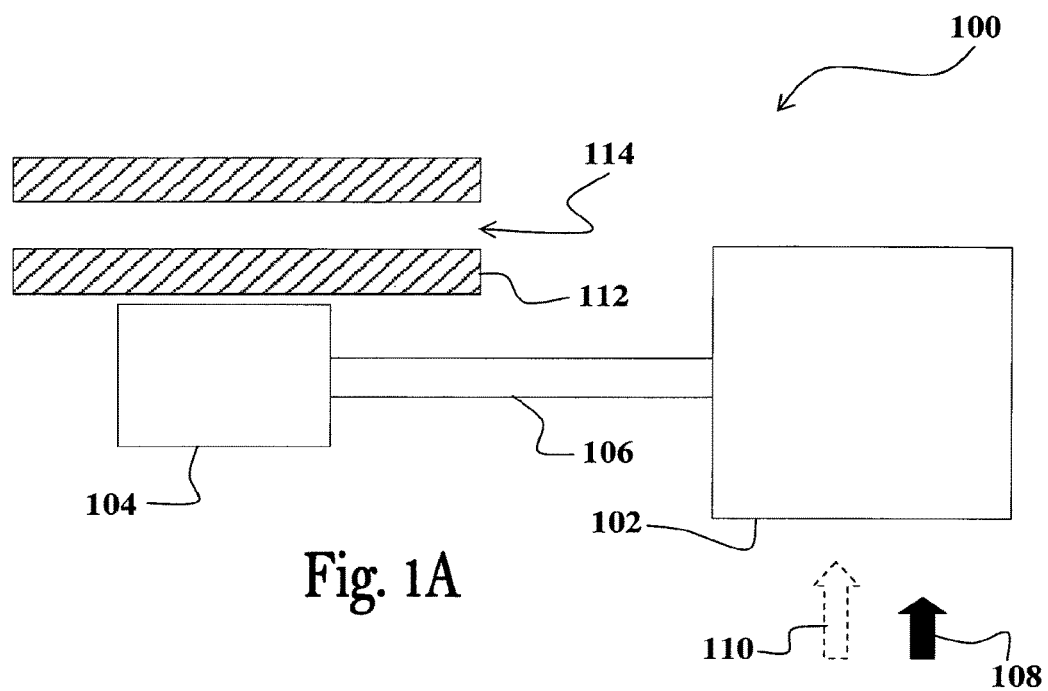
Figure 1B:
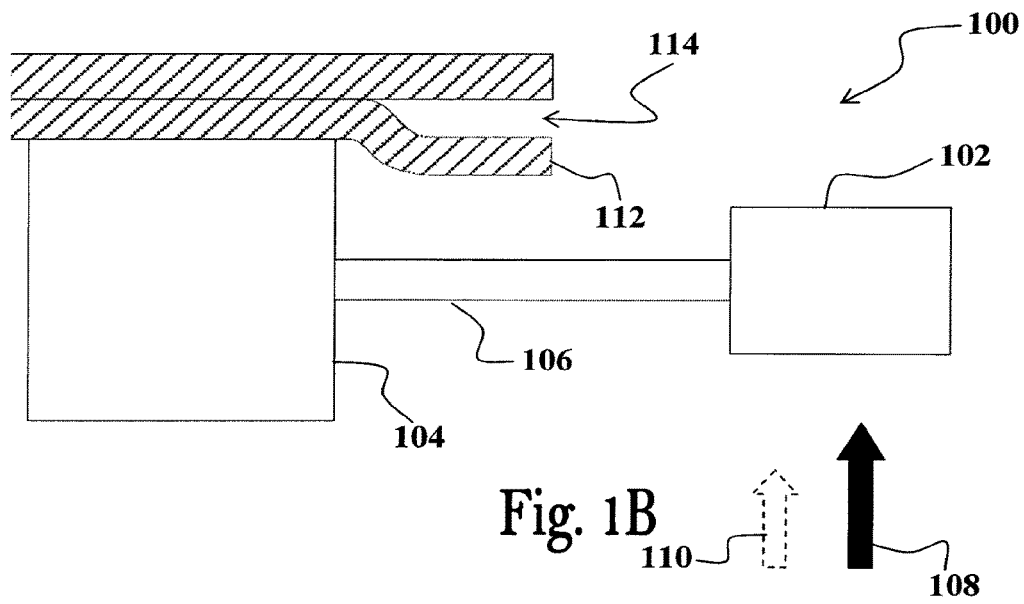

Referring now to FIGS. 1A-1B and FIGS. 2A-2B. FIGS. 1A-1B are block diagrams exemplifying a urethra-narrowing operation of an exemplary device 100 of the present invention comprising a first deformable element 102, a second deformable element 104, and a transmission element 106. In FIG. 1A the first and second deformable elements 102 and 104 are shown in a resting-state, while in FIG. 1B the first and second deformable elements are in a deformed state. FIGS. 2A and 2B illustrate possible operation of device 100 placed within a vaginal cavity of a female subject.

The first deformable element 102 is configured for being located in proximity of the cervix (150 in FIGS. 2A and 2B) of a female subject and for receiving a first pressure (an inner body pressure e.g., created by an intra-vaginal pressure, and/or an intra-abdominal pressure, and/or a contraction of the pelvic floor muscles). When the first pressure 108 is sensed by the first deformable element 102, the state of the first deformable element 102 is changed into a deformed state. The second deformable element 104 is configured for being located in the vagina contacting a section of the vaginal wall 112 near an upper section of the urethral 114, between the first deformable element 102 and the opening of the vagina. The second deformable element 104 is designed for undergoing a deformation in response to the deformation of the first deformable element 102. Because of the deformation of the second deformable element, the second deformable element 104 applies a second pressure onto the vaginal wall 112 and thereby narrows the urethra 114. The transmission element 106 has a first end connected to the first deformable element 102 and a second end connected to the second deformable element 104, and is designed for converting a deformation of the first element 102 to a deformation of the second element 104. Device 100 may be further configured for returning the first and second deformable elements 102 and 104 back into their respective resting-states when the first pressure 108 on the first deformable element 102 is extinguished.

Device 100 may be configured such that the relationship between the first and second pressures is a continuous function which may have a transfer ratio determined by attributes of the deformable elements (e.g., geometry, elasticity, etc.). The device 100 may be also configured such that the first deformable element undergoes deformation only when the first pressure is greater than some predetermined first threshold pressure 110.

In FIG. 2A the first and second deformable elements 102 and 104 are shown in a resting-state, in which no pressure, or almost no pressure, is applied over the urethral wall, while in FIG. 2B the first and second elements 102 and 104 are in their deformed states and the urethra is narrowed due to pressure applied by the second deformable element 104 of device 100.

Device 100 is therefore designed to convert a first pressure e.g., originating from an intra-vaginal pressure, and/or an intra-abdominal pressure, into a second pressure applied onto the vaginal wall (the outer side of the urethral wall) 112, in order to narrow or occlude the urethra 114. Such pressure conversion may be achieved utilizing mechanical means and/or pneumatic/hydraulic means, or combinations thereof.

In some possible embodiment of the present invention the device 100 is configured to apply pressure onto the vaginal wall 112 in a dynamic and temporary fashion, i.e. the device 100 applies pressure to the vaginal wall only in response to an increase of intra-vaginal pressure, and/or an intra-abdominal pressure. Once the first pressure on the first deformable element 102 vanishes, the first deformable element 102 and the second deformable element 104 return to their respective resting-states, and the passage through urethra 114 returns to its un-occluded or un-narrowed state. In this manner, the urethra is narrowed/occluded whenever an increase in the intra-vaginal pressure and/or in an intra-abdominal pressure occurs. Such pressure changes typically occur involuntary.

As explained above, such involuntary pressure increase causes an increase in bladder pressure. Therefore, the device of the present invention may be used to ensure that the urethra is narrowed/occluded when bladder pressure is increased, thereby preventing or decreasing occurrences of UI. At the same time, the urethra is left open, or substantially un-occluded or un-narrowed, at all other times (except for cases of voluntary contraction of the pelvic floor muscles, as will be explained below), enabling the female subject to pass urine when needed, and also preventing discomfort that may be caused if constant occluding/narrowing pressure is applied over the urethral wall.

As mentioned above, a voluntary contraction of the pelvic floor muscles may also increase the first pressure 108 on the first deformable element 102. This feature of the device 100 enables the device to be used as a tool for exercising the pelvic floor muscles, in particular if the deformations are triggered by increasing the first pressure above the first threshold pressure 110, in which cases the first deformable element 102 offers a resistance to the contractions, which needs to be overcome in order to cause deformation of the first deformable element 102. Between contractions, the first deformable element 102 returns to its resting-state, allowing for multiple contractions to be performed one after the other against the resistance provided by the first deformable element 102. Exercising in this manner may contribute to the strengthening of the pelvic floor muscles, which may in turn treat or cure conditions caused by weak pelvic muscles, such as UI, SUI, or female genital prolapse.

It should be noted that the insertion of the device 100 near the cervix may also be used in preventing at least some female genital prolapse, since the device 100—while secured inside the vagina—does not allow passage of organs from the cervix into the vagina.

In some embodiments, the first deformable element 102 is configured such that it applies a certain pressure on the vaginal wall in its resting-state. This resting-state pressure is used to keep device 100 in its correct position inside the vagina and prevents device 100 from moving out of position. Optionally, the second deformable element 104 is also configured to apply a certain pressure on the vaginal walls in its resting-state. Such resting-state pressure is not sufficient to significantly narrow the urethra, but is chosen to further prevent the device 100 from moving away from a correct position thereof and thereby to anchor it in place. In some exemplary embodiments of the present invention, the first deformable element 102 (and optionally the second deformable element 104) is shaped like a disk (or cylindrical in shape) having a circumference that is slightly greater than the circumference of the vaginal cavity, such that the first deformable element 102 clings to the vaginal wall. Alternatively, the first deformable element 102 may include a plurality of spokes extending radially outward from a center of the first element 102. The length of the spokes is chosen so that the edges of the spokes exert a certain pressure on the vaginal wall, enabling device 100 to cling to the vaginal wall and be kept in its proper position.

It should be noted that the threshold pressure may be determined according to intra-vaginal and/or intra-abdominal pressures measured while a female or test subject is performing certain activities that may cause involuntary loss of urine. A study (Johnson, Rosenbluth, Nygaard, Parikh, Hitchcock, "*Development of a novel intra-vaginal transducer with improved dynamic response*", Biomedical Microdevices (2009), Vol. 11, number 6, pp. 1213-1221) has shown the following intra-vaginal pressures measured in twelve test subjects during the activities indicated in table 1 below.

TABLE 1

| Activity | Range of intra-vaginal pressures (cm H$_2$O) | Median intra-vaginal pressure (cm H$_2$O) |
| --- | --- | --- |
| Crunch Sit-ups (holding breath) | 7.1-75.8 | 23.9 |
| Crunch Situps (breathing) | 6.7-75.0 | 12.4 |
| Standing at rest | 15.0-28.5 | 24.0 |
| Standing from chair | 23.7-38.8 | 32.3 |
| Lifting 15 lbs from counter to upper shelf | 28.1-56.7 | 38.9 |
| Lifting 15 lbs from floor to counter | 31.0-91.6 | 44.7 |
| Rise from floor (leg swing) | 44.6-100.0 | 54.5 |
| Rise from floor (side roll) | 30.8-86.1 | 45.3 |
| Jogging in place | 37.4-85.7 | 55.1 |
| Lifting 30 lbs from counter to upper shelf | 47.4-80.6 | 60.3 |
| Lifting 30 lbs from floor to counter | 35.3-100.2 | 60.2 |
| Lifting 45 lbs from floor to counter | 52.1-136.0 | 70.9 |
| Sharp cough | 49.7-133.7 | 98.0 |

Therefore, in possible embodiments of the present invention the device 100 can be designed such that the threshold pressure is a selected intra-vaginal pressure within the range between 6.7 cm H$_2$O and 52.1 cm H$_2$O. Optionally, several devices according to the device 100 can be produced having different threshold pressures, such that the female subject can be provided with a device sporting a threshold pressure suitable for her specific physiological needs.

Some UI-inducing activities (such as laughter, sneezing, or cough) may generate successive pulses of intra-vaginal or intra-abdominal pressure increases, each pulse immediately following the preceding pulse. If the reaction of the device 100 is slow in one of such pulses, some urine may escape through the urethra, notwithstanding the presence of the device 100.

Therefore, in some embodiments of the present invention, the conversion of the deformation of the first deformable element to the deformation of the second deformable element is quicker than the return of the first and second deformable elements to their resting-states. In this manner, the urethra is kept narrowed/occluded for a period following the drop of the first pressure. Optionally, the device 100 may be configured such that the deformable elements restore their resting-states following drop of the first pressure 108 below some predetermined second threshold pressure. Therefore, if the female subject has a coughing fit, for example, the urethra will be narrowed by the second deformable element's continuous pressure throughout the fit, and will not open between coughs. Device 100 may be configured such that after a certain period since the end of the coughing fit, the first and second deformable elements return to their respective resting-states, and the urethra becomes un-narrowed/un-occluded.

In some embodiments of the present invention, the magnitude of the second pressure is related to the magnitude of the first pressure 108 (for example, the second pressure being a growing function of the first pressure, or the second pressure being equal to the first pressure). Since the first pressure 108 is typically a growing function of the intra abdominal and or vaginal pressure, this feature enables the device 100 to modulate the urethral pressure according to the corresponding intra abdominal and or vaginal pressure. For example, a certain activity, such as a sharp cough typically causes a relatively large increase in intra-abdominal, intra-vaginal, and bladder pressure. Consequently, the device 100 quickly converts the large first pressure to a large second pressure, which corresponds to a large urethral pressure required to prevent urine escape. Another activity, such as standing at rest, causes smaller intra-vaginal, intra-abdominal, and bladder pressures, and therefore the device 100 applies a smaller second pressure to the urethral wall, and a smaller urethral pressure (large enough to prevent urine escape, but not so large as to cause added discomfort) is achieved. The pressure modulation feature of the device 100 ensures that urine does not escape, while reducing discomfort caused by unnecessarily high pressure on the urethra.

Figure 3A:
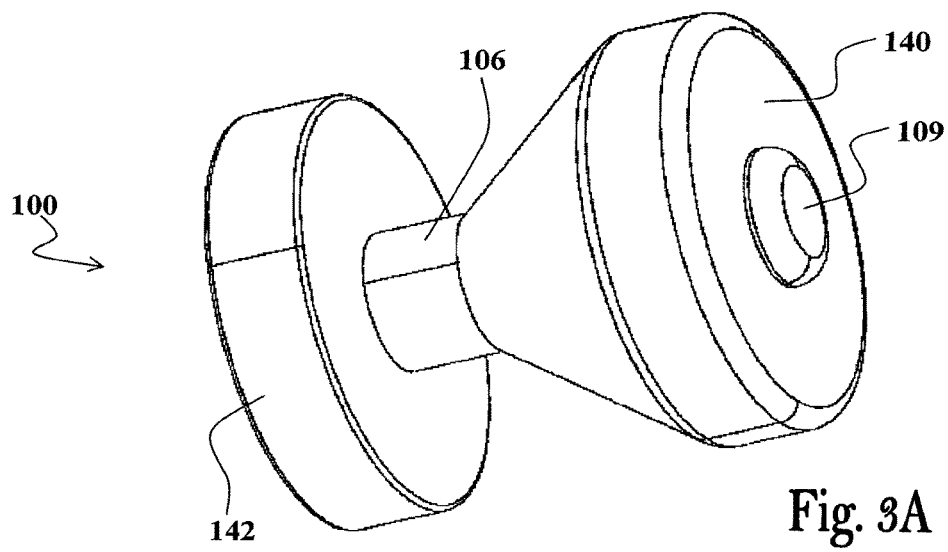
Figure 3B:
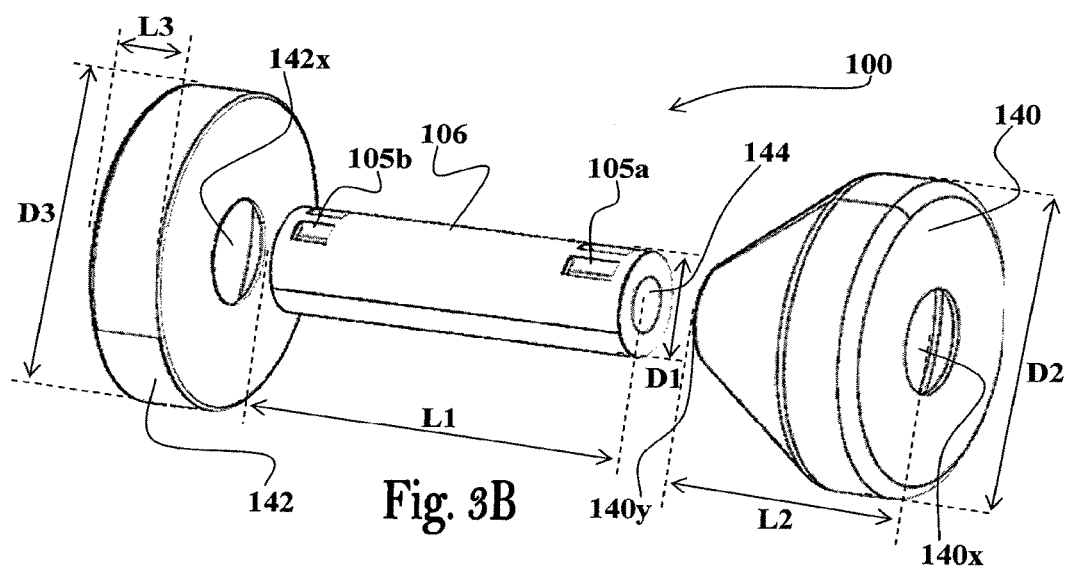

Referring to FIGS. 3A to 3C, an embodiment of the present invention is shown, wherein the first and second deformable elements of device 100 are inflatable and deflatable balloons. FIG. 3A illustrates an assembled device 100, FIG. 3B and FIG. 3C illustrate device 100 in an unassembled form, and FIG. 3D illustrates a non-limiting example of a shape of the first balloon.

In FIGS. 3A to 3C, the first deformable element of the device 100 includes a first deformable balloon 140, the second deformable element of the device 100 includes a second deformable balloon 142, and the transmission element 106 includes at least one hollow channel 144. The device 100 includes a fluid contained within the first balloon 140, the second balloon 142, and the hollow channel 144. The first balloon 140, the second balloon 142, and the channel 144 are in hermetic fluid communication with each other via respective openings 105a and 105b. The opening 105a allows fluid flow between the first balloon 140 and the channel 144, and the opening 105b allows fluid flow between the second balloon 142 and the channel 144. Therefore, when the first balloon 140 deforms (is deflated) by the first pressure, some fluid travels from the first balloon 140 to the second balloon 142 via the channel 144. In this manner, the second balloon 142 undergoes a deformation (inflation), which causes the second balloon 142 to apply a pressure to the vaginal wall and thereby to narrow or occlude the urethra.

The device in some possible embodiments of the present invention may be configured to transfer the pressure to the second balloon 142 only when the first pressure is greater than some predetermined threshold pressure. In such possible embodiments the material composition and geometry of the balloons 140 and 142 affects the magnitude of threshold pressure, as well as the relation between the first and second pressure. For example, if the first balloon 140 is made of a rigid material, the threshold pressure above which the first balloon is deformed (deflated) is substantially large. Conversely, a highly flexible material of the first balloon 140 reduces the threshold pressure. Furthermore, if the material or thickness of the first balloon 140 renders it to be more rigid than the second balloon 142, a small deflation of the first balloon 140 will correspond to a large inflation of the second balloon 142—causing a greater second pressure to be applied to the vaginal wall. Conversely, if the material or thickness of the second balloon 142 renders it to be more rigid than the first balloon 140, a large deflation of the first balloon 140 can cause a small inflation of the second balloon 142.

For example, first balloon 140 may be a type of non-compliant balloon designed to respond to pressure changes which are greater than the predetermined threshold pressure. Accordingly, the second balloon 142 may be a type of compliant, or semi-compliant balloon, such that pressure delivered thereto from first balloon 140 through the transmission element 106 is translated into inflation of second balloon 142, and correspondingly, into application of pressure over the vaginal wall. These properties can be achieved by adjusting the balloons geometry and thickness and by using different rigidity of materials. However, as described hereinabove, the device 100 may be configured such that any deformation of the first balloon 140 simultaneously results in deformation of the second balloon 142, and in this case both the first and the second balloons may be implemented by types of compliant, or semi-compliant, balloons.

The volume of the first and second balloons in their resting-states is also an important factor which establishes the relation between the first and second pressures. For example, if the first balloon 140 in its resting-state has a greater volume than that of the second balloon 142 in its resting-state, and the two balloons have the same elasticity, then a small relative deflation of the first balloon 140 can correspond to a large relative inflation of the second balloon 142.

Lastly, the shape and manner of deformation of the first and second balloons also affect the relation between the first and second pressures. For example, if the second balloon 142 is cylindrical, and inflation thereof causes only an increase in its diameter but does not increase its length, then the second pressure on the vaginal wall will be somewhat large for a certain first pressure, since the second pressure is a circumferential pressure. On the other hand, if inflation of such a cylindrical balloon 142 includes both radial expansion and axial lengthening, then the circumferential pressure on the urethra will be somewhat smaller, for the same first pressure.

The geometry of the balloons 140 and 142 in their resting-states is chosen such that at least the first balloon 140 clings to the inner vaginal wall 146, in order to ensure that the device 100 remains at a suitable position thereinside for a desired period of time—for example, a few hours, a few days, a few weeks, or more.

In a variant, the first balloon 140 (and optionally the second balloon 142 as well) has a circumference that is at least slightly larger than the circumference 148 (shown in FIG. 3D) of the inner vaginal wall 146 near the cervix 150. In this manner, a pressure is exerted by the inner vaginal wall 146 on the first balloon, causing a friction between the first balloon 140 and the inner vaginal wall 146. The friction helps keeping the first balloon 140 in place. Optionally, the first balloon 140 and the second balloon 142 each have a cylindrical portion, as seen in FIGS. 3A to 3D.

In an embodiment of the present invention, as shown in FIG. 3D the first balloon 140 has a cylindrical section 140a on a proximal side thereof (i.e., proximal side meant to be located proximal to the cervix), and a frusto-conical section 140b on a distal side thereof. In the frusto-conical section 140b, a cross sectional area of the first balloon 140 gradually increases along the central axis 152 of the first balloon as a distance from the second balloon 142 increases. The presence of the frusto-conical section 140b supports the device 100 in the vagina by creating a combined pressure vector (the sum of the vectors $P_1$, $P_2$, $P_3$, and $P_4$) on the first balloon 140 that is directed inward toward the first balloon's center and toward the cervix 150, ensuring that the device 100 remains anchored in place.

In some embodiment of the present invention the balloons 140 and 142 are at least partially made of an elastic, deformable material that is preferably biocompatible, such as, but not limited to, Poly-melt, TPR silicone, TPE (thermoplastic elastomer), TPR (Thermoplastic rubber), PVC, food-grade vinyl, Polyurethane, Medical Grade Silicone, silicone, AT-10 resin, polyisoprene, Nylon elastomers, latex, nitrile, rubber, or combinations thereof. The transmission element 106 is made of a material that is essentially non-deformable by a pressure applied thereto by the fluid inside the hollow channel 144. Any rigid, semi-rigid, elastic or semi-elastic, biocompatible material (e.g., types of biocompatible plastics, polymers, metals, metallic alloys, stiff rubbers) may be suitable for the manufacture of the transmission element 106. The fluid contained in the device 100 and transmitted between the balloons 140 and 142 may be a gas or a liquid, such as, but not limited to, air, water, distilled water, physiologic solution (water with 0.9% NaCl), hypertonic solution (water with 3% NaCl), and suchlike. In one possible embodiment of the present invention, the fluid is a non-compressible liquid, such that all of the fluid expelled from the first balloon 140 is used for the inflation of the second balloon 142. In this manlier, there is no pressure loss in the conversion of the first pressure on the second pressure. However, in possible embodiments of the present invention gases (e.g., air) may be used in device 100 for transferring pressure between the balloons. The balloons may be adhered to the transmission element (e.g., by a type of adhesive glue), or alternatively be integral with the transmission element.

In possible embodiments of the present invention variety of coatings are applied on the surface of one, or both, of the balloon(s) to enhance or change certain properties and meet implementation requirements. Such balloon coatings may include for example the following coatings: Lubricious coatings (hydrophylic and hydrophobic); Abrasion and puncture resistant coatings; Tacky or high friction coatings; Drug release coatings; silicon coating for balloons made of other materials, and combinations thereof.

Referring now to FIG. 3B, according to a non-limiting example, the transmission element 106 is cylindrical in shape and has a $D_1$ diameter, optionally below 3 cm, optionally between 1 cm and 2 cm. The length $L_1$ of the transmission element 106 may generally be between 2 cm and 7 cm. In its inflated resting-state the first balloon 140 is in a shape of a cylinder having a first aperture 140x at a first edge thereof and a second aperture 140y at a second edge thereof, the cylinder being optionally capped by a frusco-conical section. The first and second apertures 140x and 140y are configured for being traversed by the transmission element 106 when the first balloon 140 is sealably mounted on the transmission element 106. When in resting-state, the first balloon 140 has an outer diameter $D_2$, optionally in the range between 1 cm and 8 cm (optionally between 3 cm and 5 cm), and length $L_2$ optionally between 1 cm and 5 cm. The first and second apertures 140x and 140y of the first balloon 140 are designed to sealably fit over the transmission element 106.

In this example, the second balloon 142 is of cylindrical shape in its resting-state, having a first aperture 142x at a first edge thereof and a second aperture 142y (shown in FIGS. 4A-4C) at a second edge thereof. The first and second apertures 142x and 142y are configured for being traversed by the transmission element 106 when the second balloon 142 is sealably mounted thereover. In its resting-state, the outer diameter $D_3$ of the second balloon is optionally not greater than 8 cm, but may be between 1 cm and 4 cm, and the length $L_3$ of the second balloon 142 may generally be between 0.5 cm and 4 cm. The first and second apertures 142x and 142y of the second balloon 142 are designed to sealably fit over the transmission element 106. Therefore the total length of the device 100 may generally be in the range between 3 cm and 8 cm, or optionally between 4 cm and 6 cm.

All of the abovementioned parameters and substances are given by way of example only, and may be changed in accordance with the differing requirements of the various embodiments of the present invention. Thus, the abovementioned parameters and substances should not be construed as limiting the scope of the present invention in any way. In addition, it is to be appreciated that the different balloons, tubes, channels, and other members, described hereinabove and hereinbelow may be constructed in different shapes (e.g. having oval, square, etc. form in plain view) and sizes from those exemplified herein and shown in the Figs.

FIG. 3C illustrates an embodiment of the device 100 wherein the transmission element 106 is capped by two caps (generally 109), each cap 109 being sealably attached to an edge of the transmission element 106.

Various exemplary embodiments of the present invention will be now described with reference to FIG. 4 to FIG. 17, in which the first and second balloons, 140 and 142 respectively, are sealably attached over an external surface of a transmission element 106. In these examples the transmission element 106 includes a hollow tube having one or more channels and one or more lateral apertures (105a and 105b) on wall sections thereof near each of its ends for providing fluid passage between the balloons and the interior of the transmission element 106.

Figure 4A:
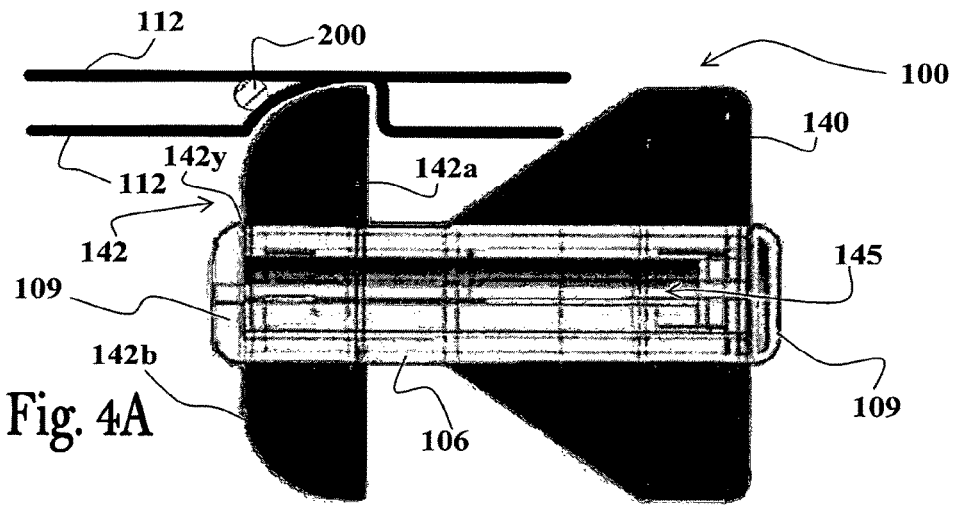
Figure 4B:
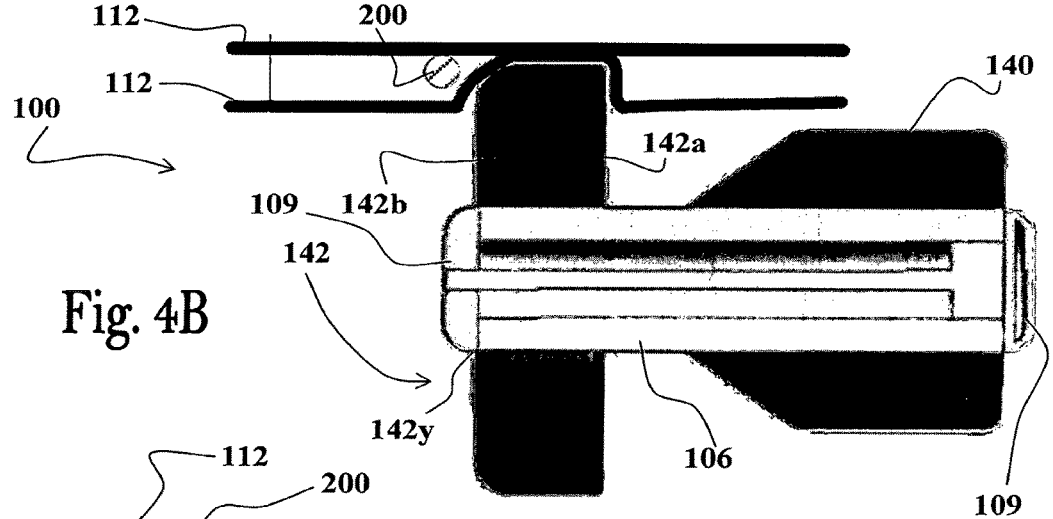
Figure 4C:
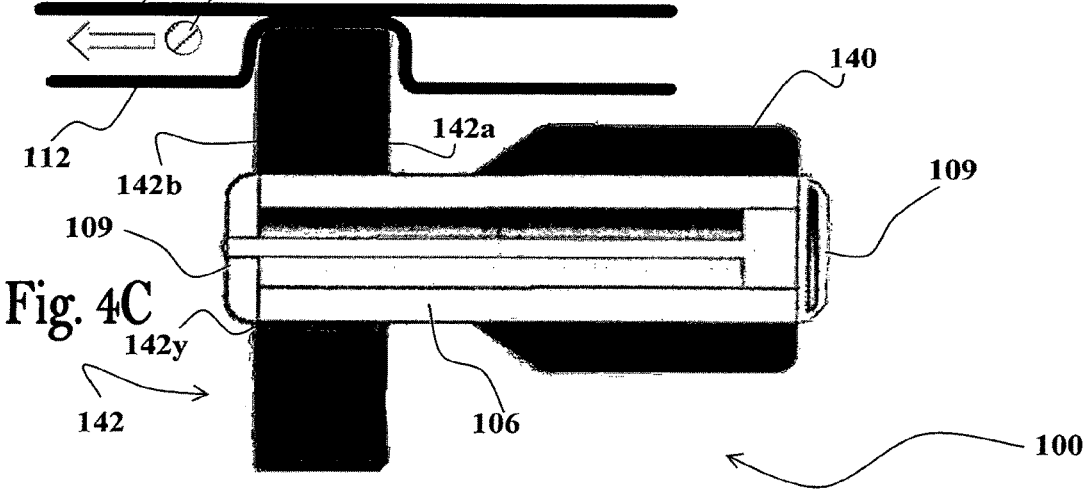

Referring to FIGS. 4A to 4C, an embodiment of the present invention is shown, in which the device 100 is used to expel an infectious agent from the urethra.

The device 100, in some embodiments of the present invention, is capable of expelling foreign materials, such as infectious agents out of the urethra. In this manner, UTI may be prevented. The second balloon 142 of the device 100 of FIGS. 4A to 4C is designed so that an inflation thereof causes an increase of the second balloon's cross sectional area beginning at the proximal end 142a (the end closest to the cervix) of the second balloon 142 and gradually propagating in time along a central axis of the second balloon 142 toward the distal end 142b of the second balloon 142. This creates a directional pressure on the urethra, propagating toward the exit of the urethra along the longitudinal axis of the urethra. In this manner, the second balloon 142 applies the second pressure to a progressively longer portion of the vaginal wall 112 and expels an infectious agent 200 out of the urethra 114.

In FIG. 4A, as the first pressure is applied to the first balloon 140, the proximal end 142a of the second balloon 142 undergoes an initial inflation. In FIG. 4B, the first pressure causes the first balloon 140 to further deflate, causing a further inflation of the second balloon 142. As can be seen, the increase of the cross sectional area (or diameter) of the second balloon 142 has propagated from the proximal end 142a toward the distal end 142b of the second balloon 142. The infections agent 200 in the urethra 114 was forced to move outward. In FIG. 4C, the deflation of the first balloon 140 and the inflation of the second balloon 142 are complete, as the distal end of the second balloon is fully inflated. Because of the directional pressure applied by the second balloon 142 to the vaginal wall 112, the infectious agent 200 is imparted a certain velocity 202 toward the exit of the urethra.

It should be noted that the device 100 operates to expel foreign materials when the first balloon 140 is deflated. This deflation may be a result of an involuntary increase of intra-vaginal and/or intra-abdominal pressure, or may be controlled by a voluntary contraction of the pelvic floor muscles. Females suffering from UTI, or prior to the disease to be used as prophylaxis, therefore may voluntarily contract their pelvic floor muscles several times in a day, in order to cause the device 100 to expel any foreign material that may be present in the urethra.

The directional inflation of the second balloon 142 may be achieved by designing the proximal end 142a of the balloon to be rigid, while the rest of the second balloon 142 is made deformable, or gradually deformable along its length. This can be attained by manufacturing the proximal end 142a with a first rigid material and the rest of the second balloon 142 with an elastic material. Alternatively, a single material may be used to manufacture the whole second balloon 142, such that the proximal end 142a is having a thicker layer of material and therefore being more rigid. In another embodiment, rigid or semi-rigid supports may be joined to the proximal end 142a of the second balloon, as will be explained below, with reference to FIG. 7 and FIG. 8.

Figure 5A:
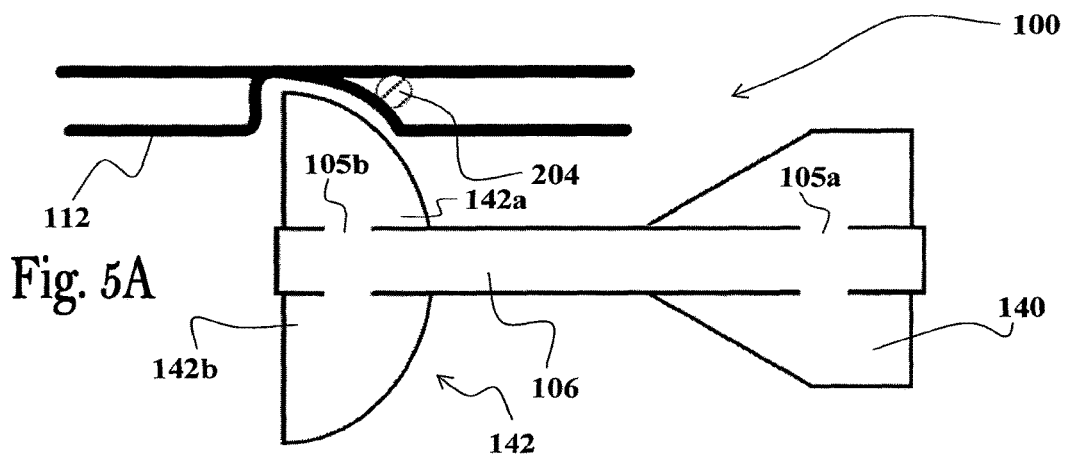
Figure 5B:
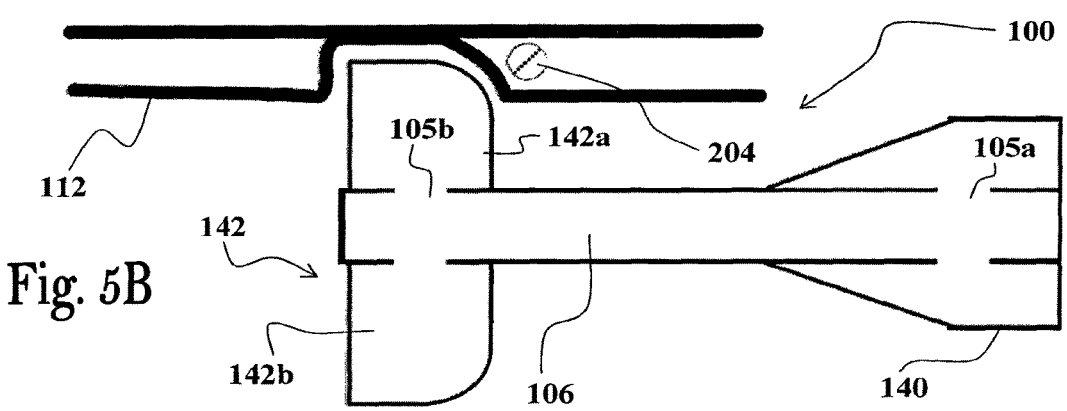
Figure 5C:
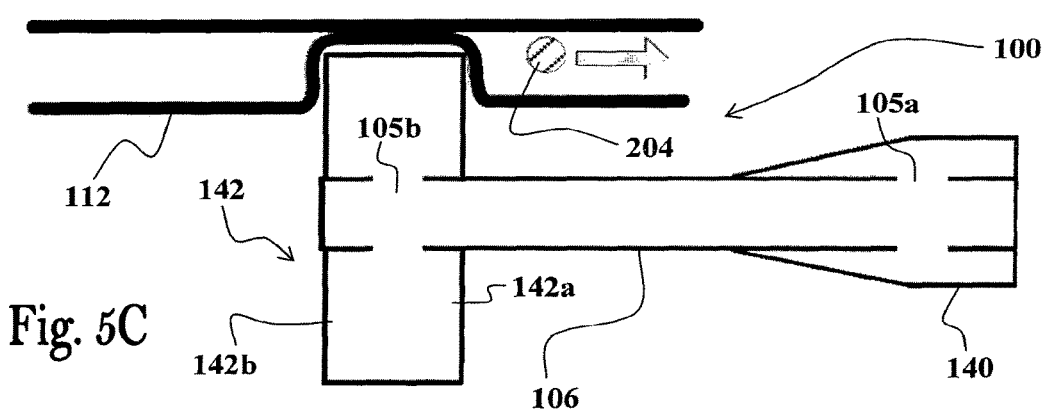
Figure 5D:
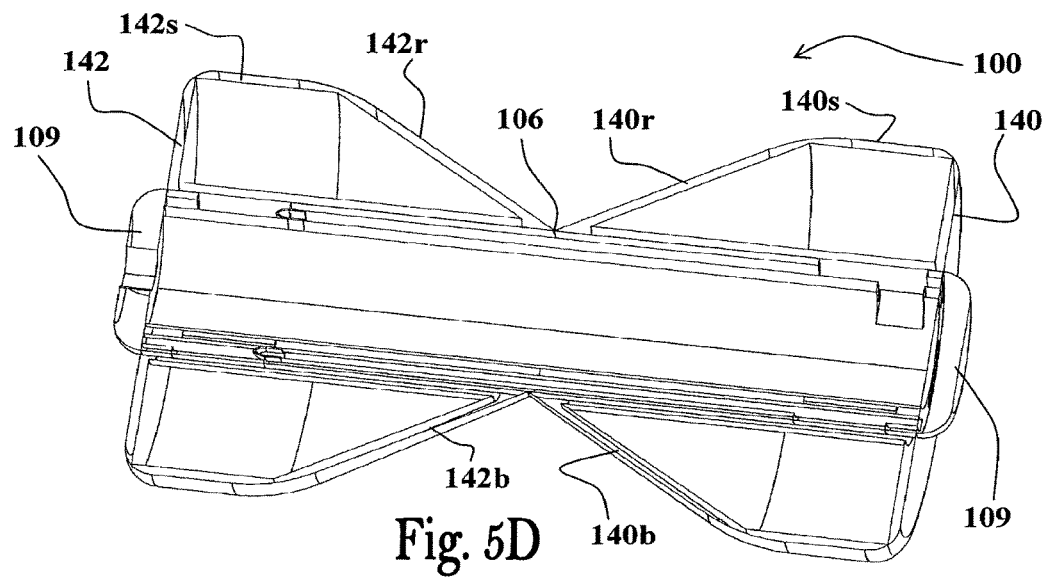

Referring to FIGS. 5A to 5C, an embodiment of the present invention is shown, in which the device is used to return some urine that may have escaped the bladder back into the bladder.

The device 100 shown in FIGS. 5A to 5C is similar to the device 100 of FIGS. 4A to 4C, except for the fact that in FIGS. 5A to 5C the directional inflation of the second balloon 142 is in the opposite direction, i.e. from the distal end 142b to the proximal end 142a of the second balloon. This creates a directional pressure on the vaginal wall 112, gradually propagating toward the bladder along the longitudinal axis of the urethra. In this manner, urine particles 204, that may have escaped the bladder before are imparted a velocity 206 and sent back to the bladder.

One exemplary manner for achieving the directional inflation of the second balloon 142 is by manufacturing the distal end 142b of the second balloon to be more rigid than the proximal end 142a. One possible implementation of the device 100 which second balloon 142 is configured for directional inflation is exemplified in FIG. 5D. In this example, both balloons 140 and 142 have a cylindrical section, 140s and 142s respectively, and frusto-conical sections 140r and 142r respectively which tapers one towards the other (also referred to herein as "bowtie configuration"), wherein the frusto-conical section 142r of balloon 142 is configured to progressively inflate proximally, as exemplified above with reference to FIGS. 5A to 5C, while the frusto-conical section 140r of balloon 140 is configured for anchoring device 100 in the vaginal cavity, as described hereinabove.

Figure 6A:
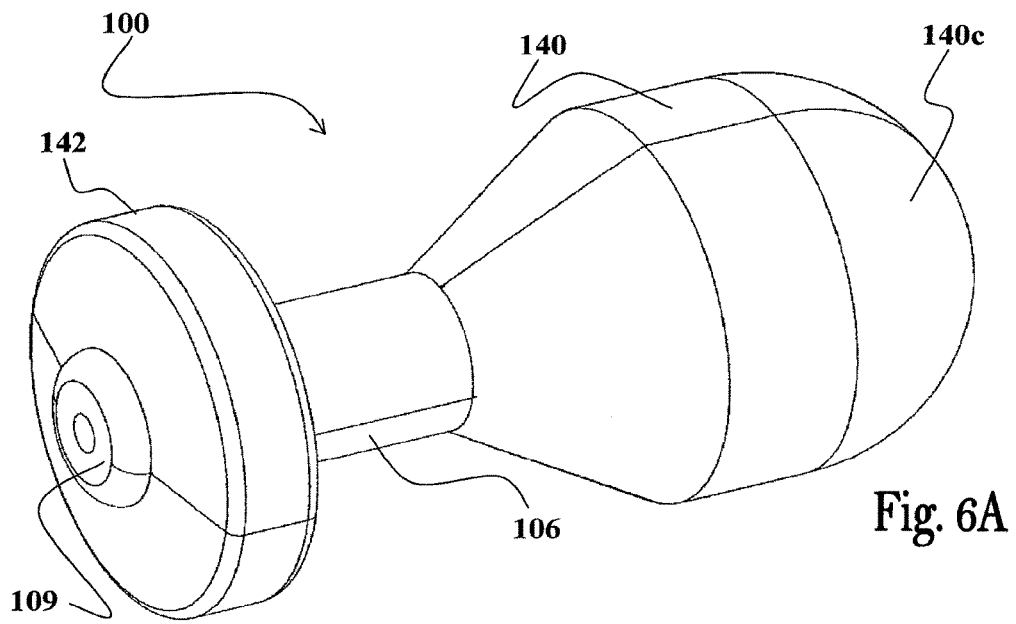
Figure 6B:
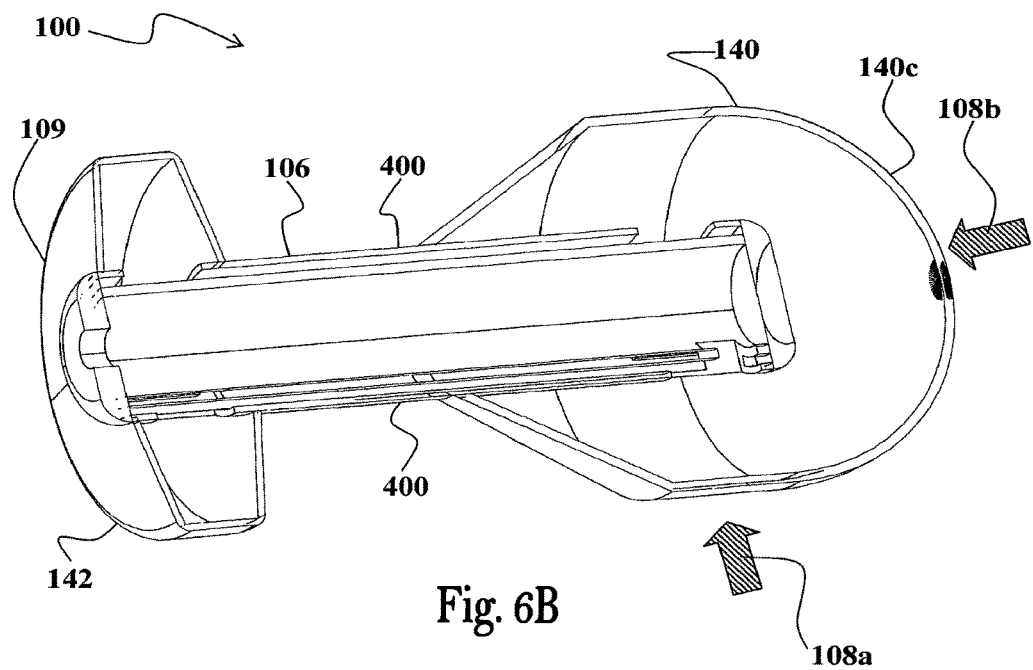
Figure 6C:
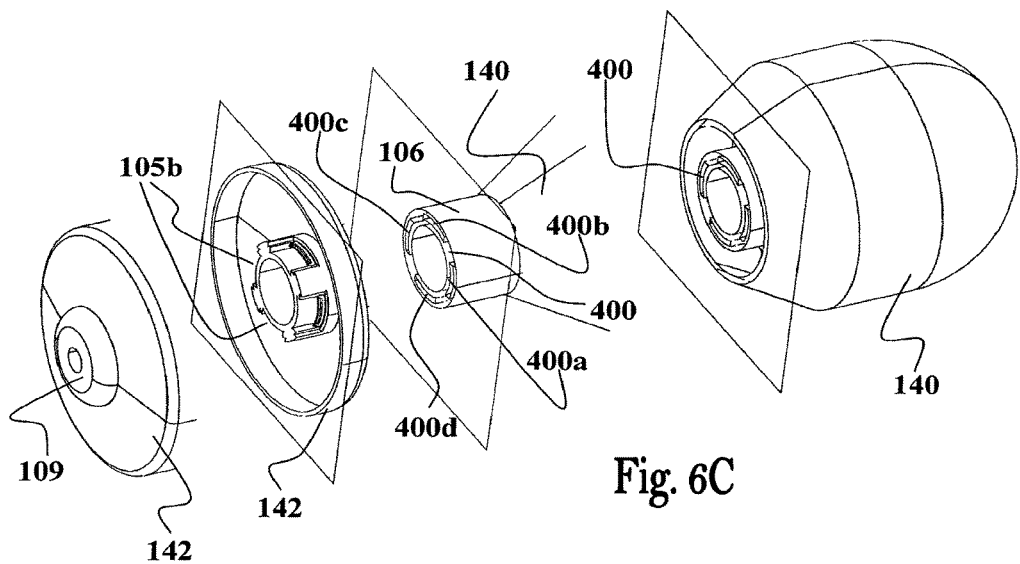

Referring to FIGS. 6A to 6C, a device 100 of the present invention is illustrated, in which the first balloon is configured for receiving both a circumferential pressure from contact with the vaginal wall and a longitudinal pressure from contact with the cervix or vaginal wall. FIG. 6A shows a perspective view of the device 100, FIG. 6B shows a side longitudinal-section view of the device 100, and FIG. 6C shows sliced cross-sectional views of portions of the device 100.

In the device 100 of FIGS. 6A to 6C, the first balloon 140 has a dome-shaped section 140c capping the first balloon 140 at a proximal side (a side facing the cervix and away from the second balloon), and extending toward the cervix. The dome-shaped section 140c is configured for pushing on the cervix, thereby supporting uterine prolapse. Furthermore, dome-shaped section 140c is able to receive a pressure 108b from an additional (longitudinal) direction, in addition to the circumferential pressure 108a. Therefore the first pressure has two components: the circumferential pressure 108a applied on the first balloon 140 by the vaginal wall, and the longitudinal pressure 108b applied on the dome-shaped section 140c of the first balloon 140 by abdominal organs pushing through the cervix, and/or by pushing the cervix towards the first balloon 140. The addition of the dome-shaped section 140c, therefore, quickens the activation of the device 100, as the first balloon 140 is subject to a pressure from an additional direction.

As seen in FIG. 6C, the outer channel 400 may be divided into a number of sub-channels 400a to 400d extending along the length of transmission element 106.

Figure 7A:
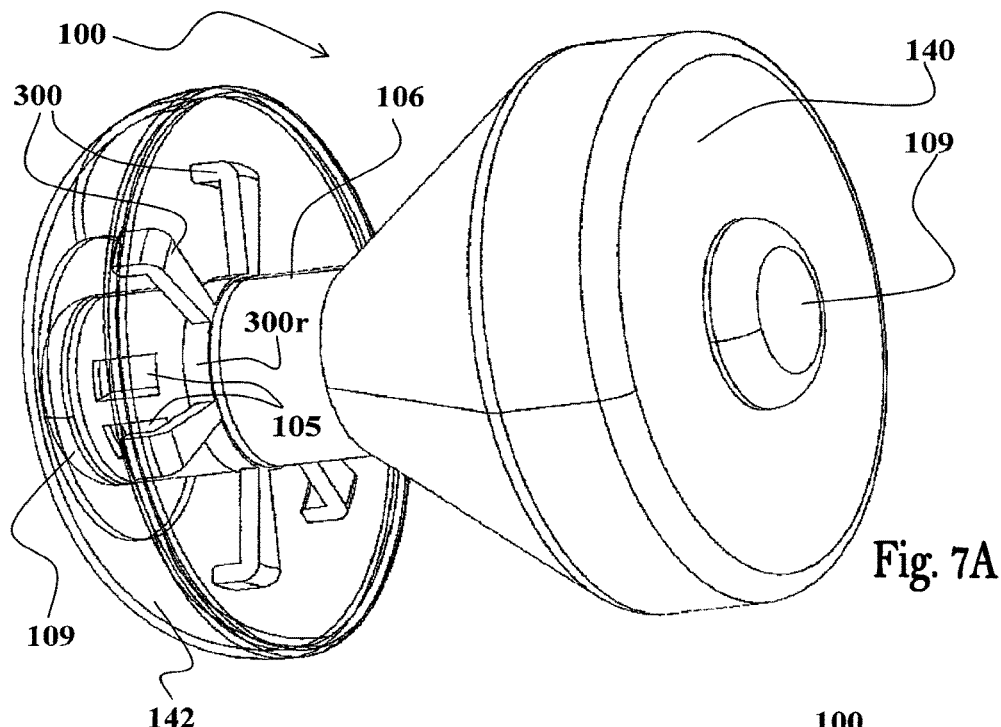
Figure 7B:
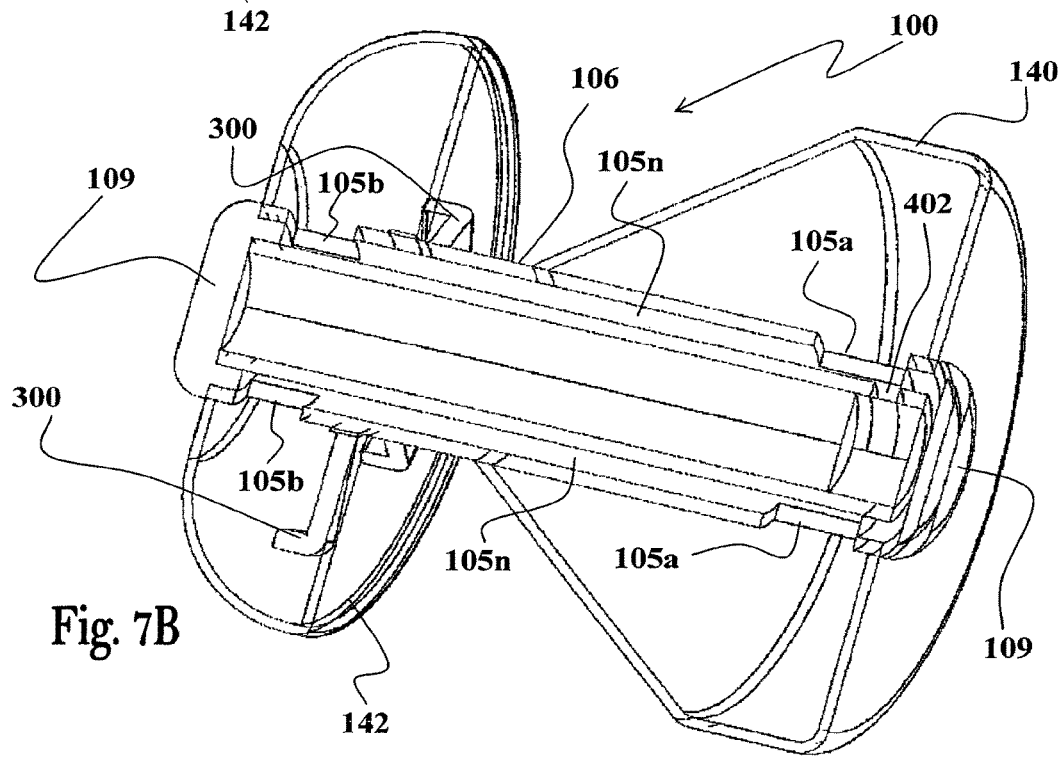
Figure 8:
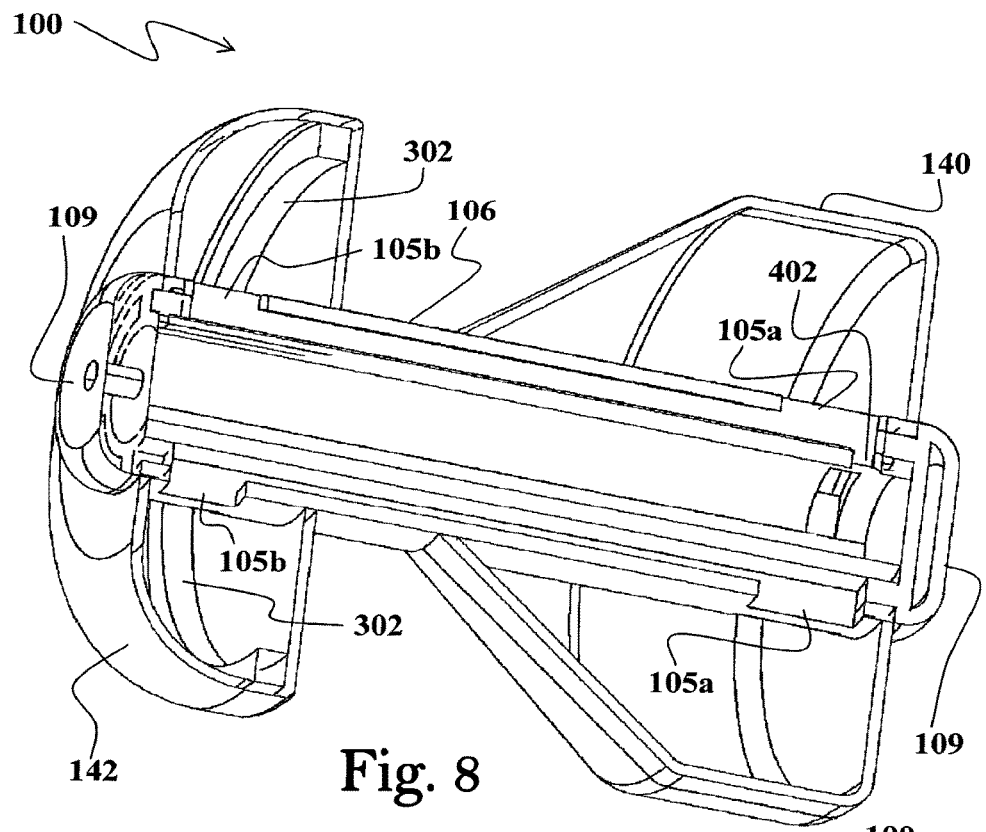
FIG. 8 illustrates a sectional perspective view of an embodiment employing a circular structural support for defining a shape of the second balloon.

Referring to FIGS. 7A-7B and FIG. 8, a device of the present invention is illustrated, in which structural supports define a shape of the second balloon.

In FIGS. 7A and 7B, the device 100 includes spoke-like structural supports 300 extending radially from the transmission element 106 and attached to a surface or ring-like element 300r at one end of the second balloon 142. In FIG. 8, the device 100 includes a circular structural support 302 defining a circumference of the second balloon 142 at an end of the second balloon 142. Optionally ring shaped support 302 is of fixed diameter. However, ring shaped support 302 may have certain flexibility (e.g., similar to rings used in the vagina for birth control). The structural supports 300 and/or 302 are used to define a shape of one end of the second balloon 142.

Though FIGS. 7 and 8 show that the structural supports 300 and 302 are placed at the proximal end of the second balloon 142, the structural supports 300 and 302 may be placed (either alternatively or additionally) at the distal end of the second balloon 142. The structural support 300 may also be placed anywhere along the length of the second balloon 142. Finally, the structural supports 300 and/or 302 may be joined to the inner surface and/or to the outer surface of the second balloon 142. Similarly, spoke-like structural supports 300 and/or circular structural support 302 may be provided on the external wall of second balloon 142. In possible embodiments of the invention both spoke-like structural supports 300 and circular structural support 302 may be provided in second balloon 142.

The structural supports 300 and/or 302 enhance the rigidity of one end of the second balloon 142, enabling a directional inflation thereof. The directional inflation can be used for expelling an infectious agent out of the urethra or returning urine into the bladder, as explained hereinabove with reference to FIGS. 4A to 4c and FIGS. 5A to 5C.

The structural supports 300 and/or 302 may be used to ensure that the second balloon 142 always remains in contact with the vaginal wall and exerts a baseline pressure on the vaginal wall before the first balloon is compressed. In this manner, the second balloon 142 clings to the vaginal wall, further ensuring that the device 100 remains in its location.

Moreover, structural supports may also be joined to the first balloon 140, in order to enhance its rigidity and raise the value of threshold pressure above which the first balloon 140 deflates.

Whether they are associated with the first or second balloon, the structural supports may form an internal skeleton that stiffens the balloon frame, and/or may constitute a base structure upon which the balloon is placed.

Figure 9:
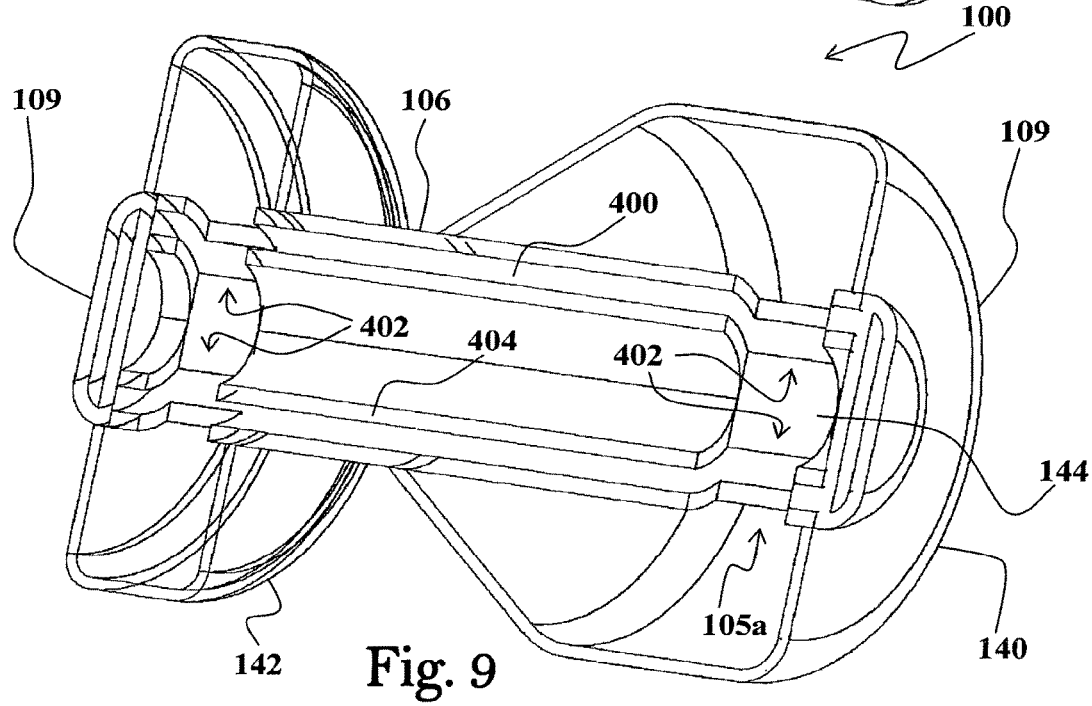
FIG. 9 schematically illustrates a sectional side view of another embodiment of the device of the present invention, in which the device comprises an inner channel surrounded by an outer channel.

Referring to the exemplary embodiment illustrated in FIG. 9, in this example the transmission element 106 of the device 100 includes an inner channel 144 surrounded by an outer channel 400. The inner and outer channels are in fluid communication with each other via one or more apertures 402 located on the inner wall 404 separating the inner channel 144 and the outer channel 400.

Referring to the exemplary embodiment illustrated in FIG. 10, in this example the transmission element 106 of the device 100 includes an outer channel 400 surrounding a solid internal rod-like element 406, which may be a part of transmission element 106.

The outer channel 400 may be divided into a plurality of compartments 400a, 400b, 400c, and 400d, as exemplified in FIG. 11A. Alternatively, transmission element 106 may be configured to provide a single passage 144 divided into a plurality of sub-channels 144a, 144b, 144c, and 144d, as exemplified in FIG. 11B.

Referring to FIGS. 12 to 15, different examples of the device 100 of the present invention are illustrated, in which fluid flow from the first balloon 140 to the second balloon 142 is quicker than the fluid flow from the second balloon 142 to the first balloon 140.

A first advantage of this feature lies in the fact that the deflation of the first balloon 140 is quickly converted into the inflation of the second balloon 142. This endures that the device 100 quickly reacts to an increase in intra-abdominal and/or intra-vaginal pressure, in order to narrow/close the urethra and prevent urine escape.

Another advantage of this feature lies in the fact that once the first pressure on the first balloon 140 is extinguished (or drops below the threshold pressure), the deflation of the second balloon is slow. In this manner the urethra is kept narrowed/occluded for a period of time which follows the drop in the first pressure. As explained above, this ensures that urine is not lost during UI-inducing activities (such as laughter, sneezing, or cough) in which successive pulses of intra-vaginal or intra-abdominal pressure rise are generated.

Figure 12:
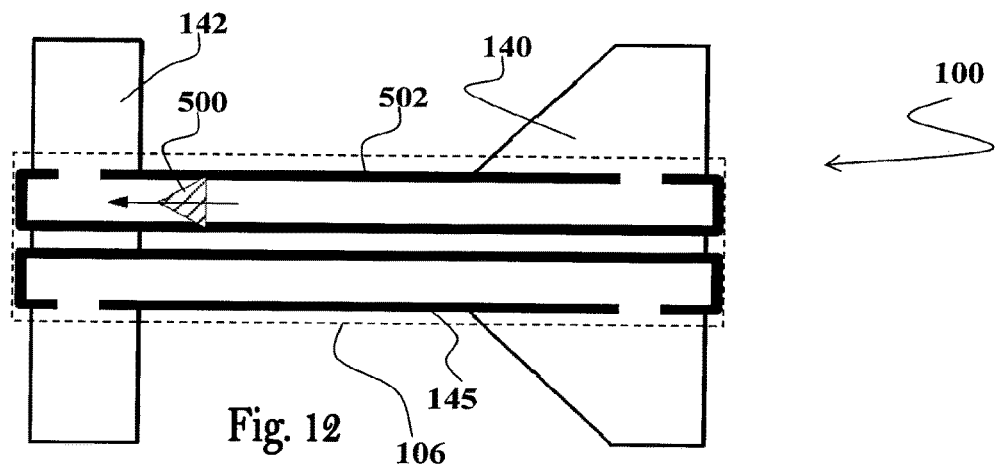

In FIG. 12, two channels (145 and 502) are included in the transmission element 106. The first channel 145 can be traversed by the fluid in both directions. The second channel 502 is associated with a unidirectional valve 500 which allows fluid passage only from the first balloon 140 to the second balloon 142. In this manner, when the first balloon 140 is deformed by the first pressure the fluid expelled from the first balloon is transmitted to the second balloon 142 via both the first channel 145 and the second channel 502, and therefore encounters little resistance in its flow. However, when the first pressure drops and the first balloon 140 starts its return to its resting-state, the fluid returning from the second balloon 142 to the first balloon 140 encounters higher resistance, since it can only flow through a narrower region defined by the first channel 145. Therefore, the deflation of the second balloon 142 is slower than its inflation. The location of the valve 500 (i.e. whether the valve 500 is located in the first or second channel), and the cross sectional areas of the first and second channels determine the speed of inflation and deflation of the second balloon 142. Valve 500 is not necessarily a unidirectional valve, for example, valve 500 may be designed to permit fluid flow in one direction and to substantially resist (or prevent) fluid flow in the opposite direction.

Alternatively or additionally, an additional valve (not shown) may be placed in the first channel 145 to prevent or substantially resist fluid flow therethrough in the direction from the first balloon 140 to the second balloon 142. Such possible embodiment may be adapted to define a first threshold pressure above which fluid flow in the direction of the second balloon 142 is permitted through the second channel 502, and a second threshold pressure above which fluid flow in the direction of the second balloon 142 is permitted through the first channel 145.

Figure 13:
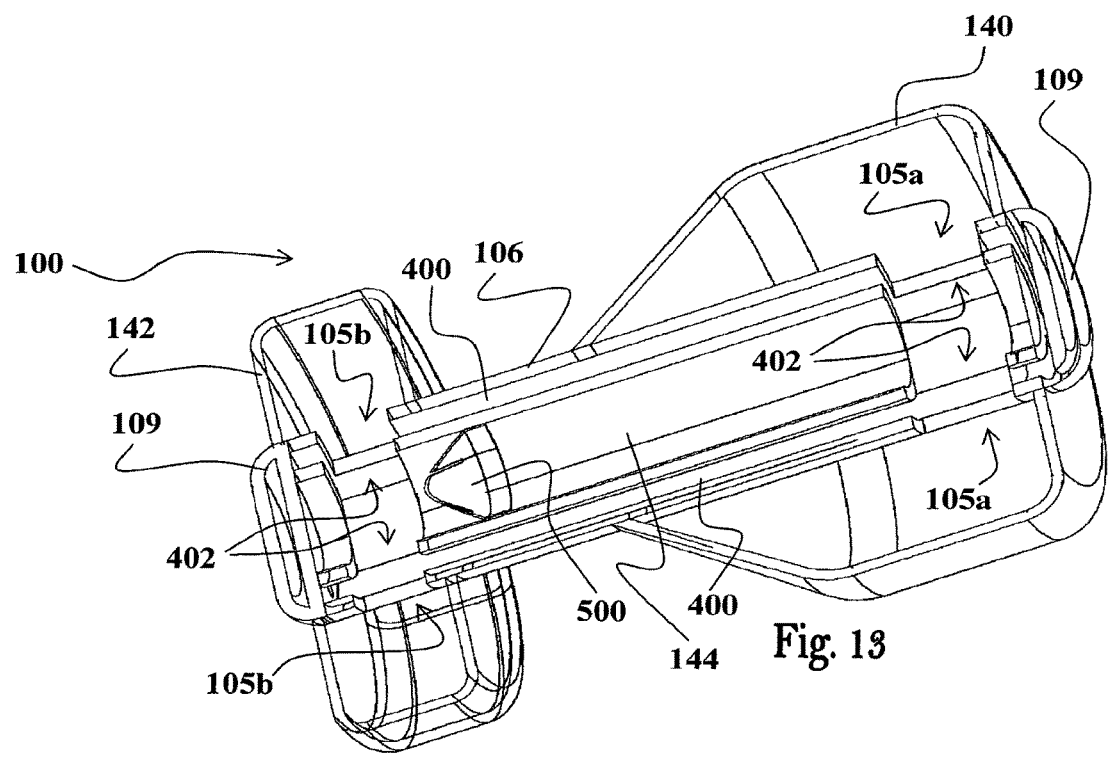

In FIG. 13, the device 100 has an inner channel 144 surrounded by an outer channel 400. A unidirectional valve 500 is placed in the inner channel 144. The valve 500 allows passage of the fluid from the first balloon 140 to the second balloon 142 through inner channel 144, but prevents (or resists) fluid flow inside inner channel 144 in the reverse direction. Therefore, fast inflation of second balloon 142 is achieved since fluid flow from first balloon 140 is enabled through both channels 144 and 400. However, since unidirectional valve 500 prevents (or resists) flow inside inner channel 144 in the direction of first balloon 140, the deflation of the second balloon 142 is carried out only through outer channel 144, and thus it is slowed. It should be noted that the valve 500 may be placed in the outer channel 400 instead of the inner channel 144. It is noted that valve 500 is not necessarily unidirectional in the sense that it may simply resist fluid flow in the direction of first balloon 140.

Figure 14:
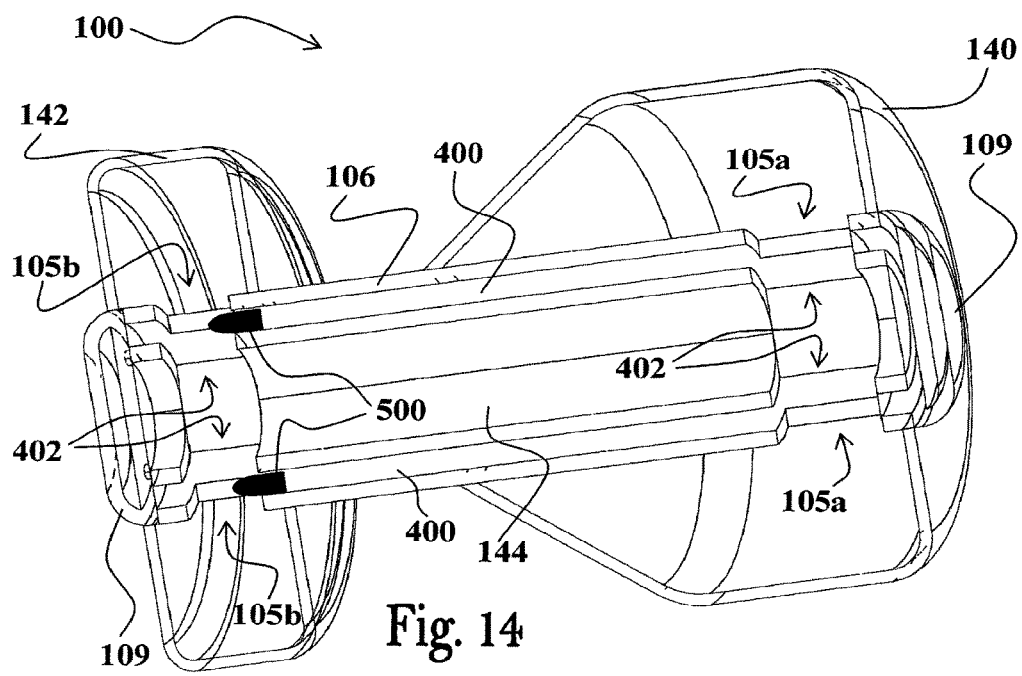

The device 100 shown in FIG. 14 is configured to permit substantial fluid flow in the direction of the first balloon 140 only via the internal channel 144. In this exemplary embodiment valve 500 is placed to cover at least part of the cross-sectional surface of the outer channel 400. The valve 500 allows passage of the fluid from the first balloon 140 to the second balloon 142, but prevents, or resists, fluid flow in the reverse direction. At the location of the valve 500 a smaller cross-sectional area of the outer channel 400 can be crossed by fluid moving from the second balloon 142 to the first balloon 140. In this manner, the deflation of the second balloon 142 is slowed.

Figure 15:
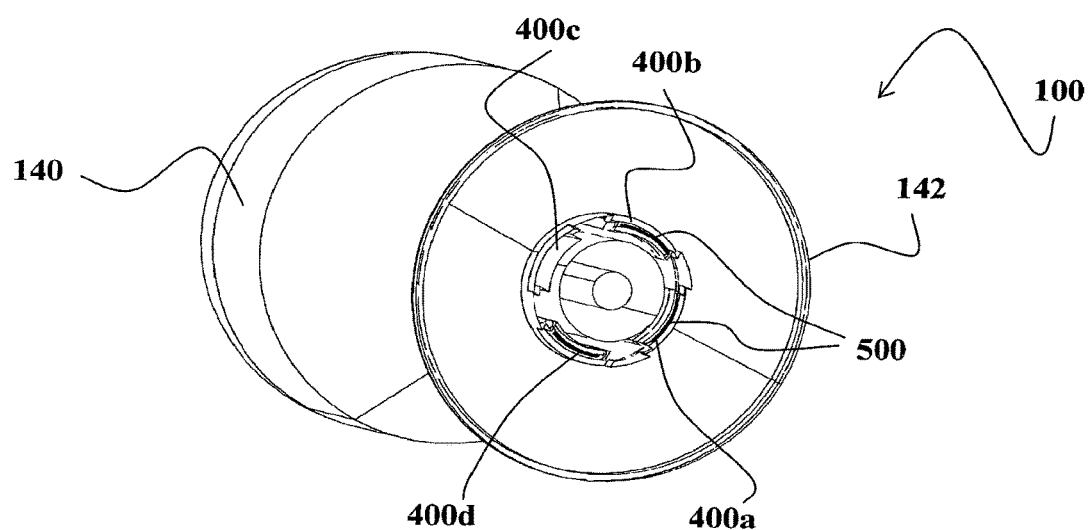

In FIG. 15, the outer channel 400 is divided into a plurality of separate sub-channels, as explained above with reference to FIG. 11A. At least one of the sub-channels includes a valve 500 which prevents, or resists, fluid flow from the second balloon 142 to the first balloon 140, and at least one of the sub-channels (e.g., 400c) does not include any such valve. In this manner, all the compartments can be used to stream fluid from the first balloon 140 to the second balloon 142, and only some of the compartments can be used to stream fluid from the second balloon 142 to the first balloon 140. In this manner, the deflation of the second balloon 142 is slowed.

Figure 16:
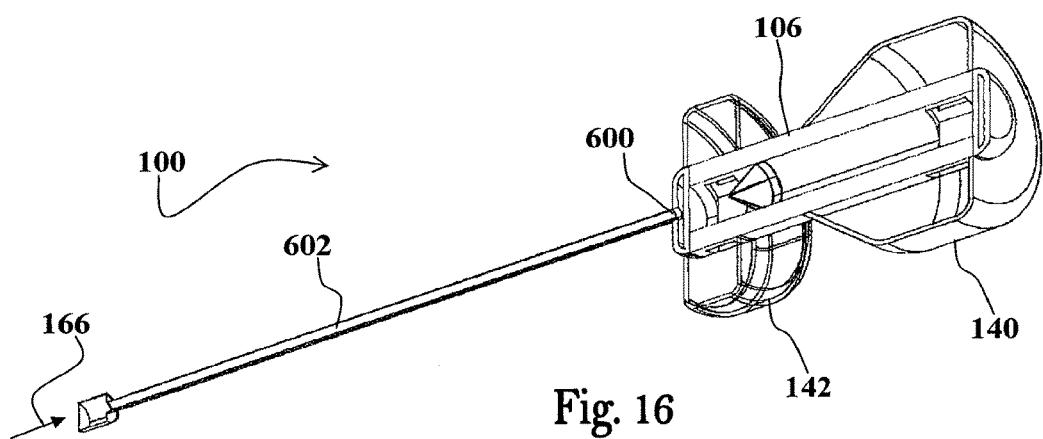
FIG. 16 is schematically illustrate a device of the present invention inflatable by an external fluid pressure source.

Referring to the exemplary embodiment illustrated in FIG. 16, showing a device of the present invention being inflatable by an external fluid source 166 via an applicator.

The device 100 includes an external valve 600 provided in flexible inflation/deflation tube 602 (also referred to herein as an applicator) associated with the transmission element 106. Flexible inflation/deflation tube 602 includes a hollow duct through which fluid can flow into the device 100 and out of the device 100. The external valve 600 allows fluid flow therethrough out of transmission element 106 only when the outer valve 600 is opened. It is noted that valve 600 may be similarly placed anywhere along flexible inflation/deflation tube 602, or at the other extremity of flexible inflation/deflation tube 602 (i.e., remote from transmission element 106).

In order to easily and comfortably place the device 100 illustrated in FIG. 16 into the vaginal cavity of a female subject, the device 100 is inserted into the vagina when both the first and second balloons are empty of fluid. In this manner friction between the device 100 and the vaginal wall is decreased during insertion. After insertion, fluid is driven through the tube into the device 100, filling the balloons such that at least the first balloon 140 (and preferably the second balloon 142 as well) exerts a desired pressure on the vaginal wall, enabling the device 100 to cling to the vaginal wall and be kept in its proper position.

In order to remove the device 100 from the vaginal cavity of the female subject, the tube 602 is inserted into the vaginal cavity in order to contact the device's outer valve 600. Once contact is made, at least some of the fluid in the device 100 is discharged into applicator 602, decreasing the contact (and pressure) between the balloons and the vaginal wall, and therefore allowing easy removal of the device 100.

Optionally, the applicator 602 is rigid or semi-rigid, so that it can be used to push the device 100 into its desired position within the vagina, and to pull the device 100 during removal of the device.

The device 100 shown in FIG. 16 has a flexible tube 602 that is used for inflation and deflation of the balloons 140 and 142 before, during or after insertion thereof into the vagina. The tube 602 has a valve 600 connected to it to introduce fluid pressure, and to maintain this fluid pressure within the device once inflated. This valve 600 can be placed at any point along the tube 602 including its distal tip (166), In this manner the applicator 602 can inflate and deflate the device from the outside of the vagina. The tube 602 may also be used for extraction of the device simply by pulling on it.

Referring to FIGS. 17A to 17D, a device 100 of the present invention is illustrated, the device 100 being inflatable by a piston travelling within the central channel.

In the device 100, the transmission element 106 includes an inner channel 144 surrounded by an outer channel 400. The inner channel 144 and the outer channel 400 are separated by a wall having an aperture 700 located near a proximal end of the transmission element 106. The outer channel 400 has at least one first aperture 105a allowing fluid passage between the outer channel and first balloon 140, and at least one second aperture 105b allowing fluid passage between the outer channel 400 and second balloon 142. The device 100 includes a piston 702 in a substantially hermetic contact with the inner wall of the inner channel 144.

Figure 17A:
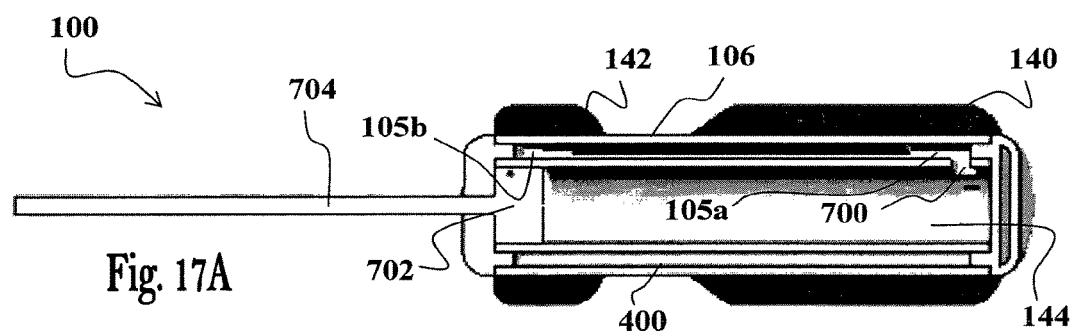

As shown in FIG. 17A, before insertion of the device 100 into the vagina, the piston 702 is at a distal end of the inner channel 144, and most of the fluid is contained within the inner channel 144. In this manner, both the first balloon 140 and the second balloon 142 are at least partially deflated.

Figure 17B:
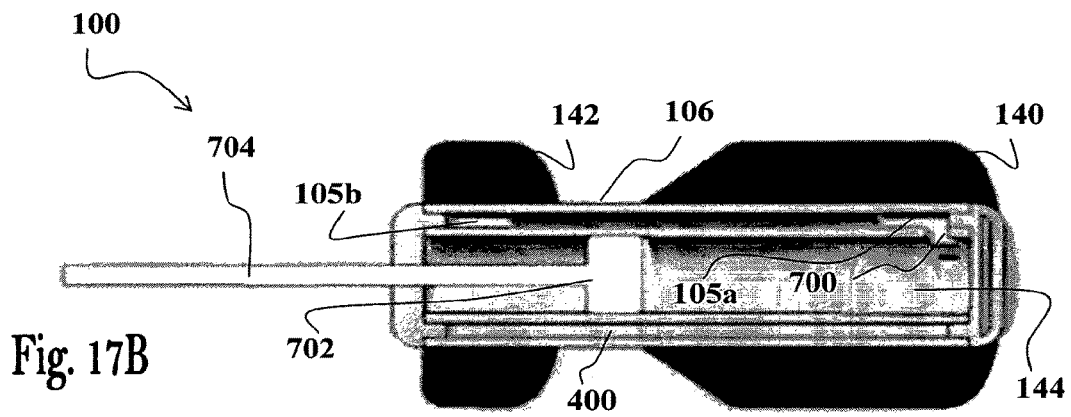
FIG. 17B and FIG. 17C show the device in intermediate stages of the inflation.
Figure 17C:
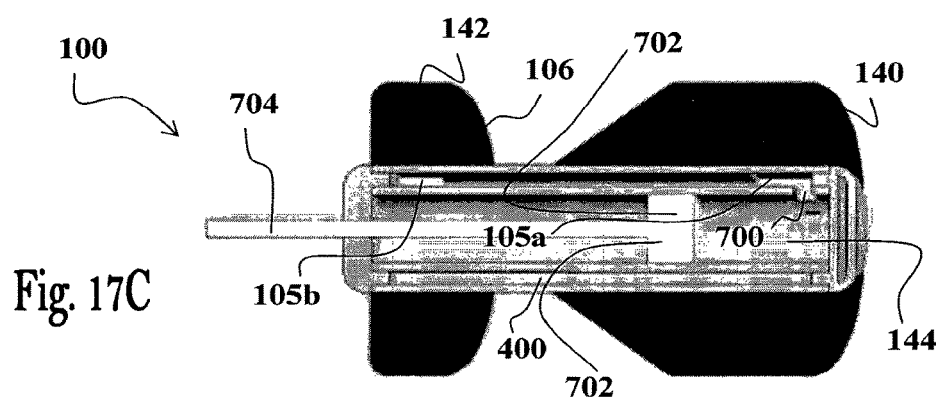

As shown in FIGS. 17A and 17B, after (or during/prior insertion) the device 100 is inserted into the vagina and placed into its desired position, the piston 702 is pushed toward the first balloon 140, and the fluid is driven from the inner channel 144 into the outer channel 400 and the balloons 140 and 142. Because of the substantially hermetic contact between the piston 702 and the inner wall of the inner channel 144, little or no fluid is to be found in the section of the inner channel 144 between the piston 702 and the distal end of the inner channel 144. As the piston 702 is pushed toward the proximal end of the inner channel 144, the fluid is driven into the outer channel 400 and into the balloons 140 and 142, thereby inflating the balloons.

Figure 17D:
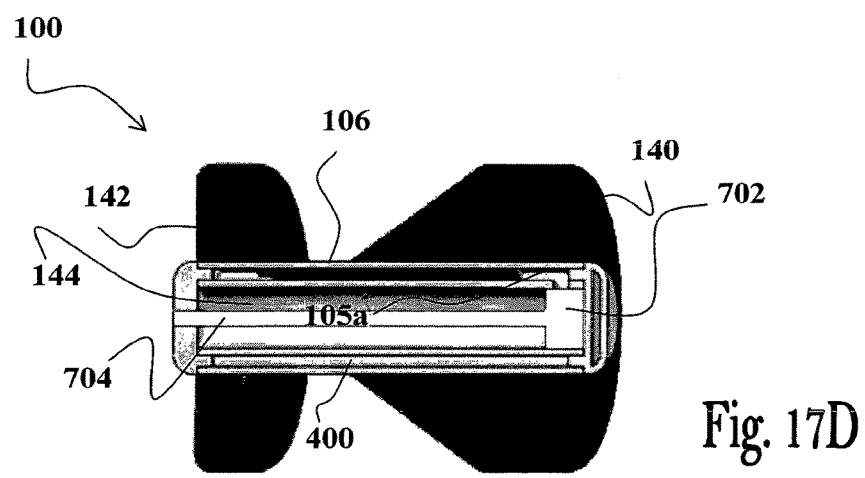

In FIG. 17D, the piston 702 is in contact with the proximal wall of the inner channel 144, and all the fluid is contained in the outer channel 400 and in the balloons 140 and 142. The balloons 140 and 142 are in their resting-states, and the device 100 is therefore ready to operate in response to an inner body stimulus (first pressure). The piston 702 also blocks the aperture 700 between the channels, ensuring that no fluid can enter into the inner channel 144. Optionally, there is provided a locking mechanism (such as a mechanical or electromagnetic mechanism) for keeping the piston joined to the proximal end of the inner channels.

For example, in one possible embodiment of the present invention a small step (not shown) is formed inside the inner channel 144 that locks the piston 702 in place once it is passed over the step and abuts the proximal wall of inner channel 144. In another possible embodiment of the present invention the device 100 is configured to allow the pressure from the outer channel 400, applied through aperture 700, to press piston 702 against the wall of inner channel 144, thereby increasing the friction between piston 702 and inner channel 144 and anchor the piston 702 in place once it abuts the proximal wall of inner channel 144.

Such piston lockage can occur because once the piston 702 reaches the proximal wall of inner channel 144 there are no forces pushing back on the piston 702. The only forces that do act on the piston 702 are the pressure from the outer channel 400 that are pushing the piston 702 towards the cylinder circumference wall, thus assisting in holding the piston 702 in place.

When the female subject wants to remove the device, if the balloons are clinging to the vaginal wall with a force greater than the friction of the piston head and the cylinder, then once the piston 702 is moved backwardly the balloons diameter is reduced, thereby releasing their cling on the vaginal wall. If in the first place the resistance of the balloons to longitudinal axial movement along the vagina is low the piston 702 will remain at the end of the inner channel 144 and the device 100 will be extracted in that position (i.e., with the piston 702 at the end of the inner channel 144).

The friction between the piston 702 and the inner channel 144 is influenced by the type of materials selected and the geometry of the elements, and used to control the pressure exerted on the circumference of the piston 702. Holding piston 702 in place can be also considered in order to create a threshold pull pressure at which the piston will move back to allow for a more comfortable extraction of the device. In order to extract the device 100 from the vagina, the piston 702 is pulled back so that the fluid leaves the balloons 140 and 142, and is stored in the inner channel 144. Therefore, in this case, the inner channel 144 is used as a fluid reservoir, and not as a transmission element.

The device 100 optionally includes a shaft 704 joined to the piston 702, and extending away from the piston toward a distal direction. The shaft 704 can be pushed and pulled to manipulate the piston 702. The piston 702 may be controlled in any other number of ways, such as, for example, the piston 702 can be pushed forward (towards the first balloon) using an integral shaft 704 connected to it, during which said shaft is introduced into the transmission element 106, once the piston 702 reaches the end the inner channel 144. Additionally or alternatively, a string or a wire (not shown) may be attached to the shaft 702 to allow for the female subject to pull it back in order to extract the device 100 (with or without moving the piston 702 as described before).

During insertion the shaft 704 can be pushed forward using an applicator before, during or after, insertion into the vagina. In another possible embodiment of the present invention relating to the insertion method of the device there is no shaft attached to the piston 702 and the piston 702 is pushed forward using an applicator, in which case extraction of the device 100 be done using a string or a wire connected to the piston 702, allowing it to be pulled back (or to pull the device back as described hereinabove).

The various embodiments of the present invention discussed hereinabove may be covered by one or more layers of absorbent materials (e.g., cotton, and/or any other suitable absorbent material as used in commercially available tampons) to implement the device in a form a tampon. In such implementations the device of the present invention may be a disposable device further functioning as a tampon.

Though in some of the embodiments of the present invention the second balloon 104 is configured to narrow an upper section of the urethra, in possible embodiments of the present invention the device 100 may be configured such that the second balloon 104 is located proximal to any section of the urethra i.e., near or remote to the urethra opening.

Various embodiments of the present invention may have further usages, such as those described in International Patent Application No. PCT/IL2011/000288 to the same inventors of the present invention. The entire disclosure of International Patent Application No. PCT/IL2011/000288 is incorporated herein by reference. For example, the device may be used for rehabilitation of stress urinary incontinence by strengthening the pelvic muscles, as a biofeedback pelvic floor muscle exerciser, for prevention and treatment of organ prolapse, to improve sexual health of the female subject, and/or for treating a pain, such as, menstrual pain, interstitial cystitis, pelvic pain, chronic pelvic pain, painful bladder syndrome or any combination thereof. The device 100 may include a biofeedback mechanism adapted to be activated upon organ prolapse.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

We claim:

1. A device for applying pressure on a vaginal wall of a female subject, said device being configured for insertion into a vaginal cavity of said female subject, the device comprising:
    a first deformable element having a resting-state and at least one deformed state, said first deformable element configured to anchor said device when in said resting-state inside the vaginal cavity and for undergoing deformation in response to an inner body pressure;
    a second deformable element having a resting-state and at least one deformed state, said second deformable element configured for undergoing deformation to apply a second pressure on said vaginal wall operable to narrow a urethral portion of said female subject; and
    a transmission element having a first end connected to said first deformable element and a second end connected to said second deformable element, said transmission element being configured for converting the deformation of said first deformable element to a deformation of said second deformable element, and for returning said first and second deformable elements to their respective resting states,
    wherein said first and second deformable elements comprise a first and a second balloon, respectively, and wherein said transmission element comprises at least one hollow channel traversable by a fluid such that said fluid can flow between said balloons therethrough, and wherein the deformation of the first balloon caused by said inner body pressure is a deflation and the deformation of the second balloon is an inflation; and
    wherein the first balloon comprises a tapering section configured to provide the anchoring in the vaginal cavity, said tapering section facing said second balloon and narrowing in the direction of the second balloon;
    and at least one support element attached to at least said second balloon.

2. The device according to claim 1, wherein the first deformable element is configured to undergo deformation whenever the inner body pressure is greater than a threshold pressure.

3. The device according to claim 1, wherein the inner body pressure is originated by at least one of: an intravaginal pressure, an intra-abdominal pressure, and a contraction of pelvic floor muscles.

4. The device according to claim 1, wherein said first deformable element is configured to be placed in proximity of a cervix of the female subject, and wherein said second deformable element is configured to be placed in contact with the vaginal wall proximal to a section of the urethra.

5. The device according to claim 1, wherein the second balloon is configured to inflate such that successive portions thereof radially expand in a gradual manner in response to the deformation of the first balloon.

6. The device according to claim 5, wherein the radial expansions define a progressive radial inflation propagating in the direction away from the first balloon.

7. The device according to claim 5, wherein the radial expansions define a progressive radial inflation propagating in the direction of the first balloon.

8. The device according to claim 1, wherein said first balloon has a dome-shaped section at an end thereof facing away from said transmission element.

9. The device according to claim 8, wherein said dome-shaped section is configured for receiving at least a portion of said inner body pressure via a contact with a uterus of the female subject.

10. The device according to claim 1, wherein said at least one support element is adapted to affect a shape of at least a portion of said second balloon.

11. The device according to claim 1, wherein said transmission element is configured such that a fluid flow rate therethrough in a direction from said first balloon to the second balloon is different from the fluid flow rate therethrough in a direction from said second balloon to the first balloon.

12. The device according to claim 11, wherein the rate of fluid flow in the direction from the first balloon to the second balloon is greater than the rate of fluid flow in the direction from the second balloon to the first balloon.

13. The device according to claim 1, wherein said at least one hollow channel comprises an inner channel surrounded by an outer channel.

14. The device according to claim 1, wherein the first balloon comprises a cylindrical section configured for receiving said inner body pressure via a circumferential contact with the vaginal wall.

* * * * *